(12) United States Patent
Lange et al.

(10) Patent No.: US 7,863,397 B2
(45) Date of Patent: Jan. 4, 2011

(54) REACTIVE AMINO-AND/OR AMMONIUM POLYSILOXANE COMPOUNDS

(75) Inventors: Horst Lange, Bochum (DE); Roland Wagner, St. Augustin (DE); Anita Witossek, Langenfeld (DE); Karl-Heinz Stachulla, Leverkusen (DE); Karl-Heinz Sockel, Leverkusen (DE); Annette Moeller, Bonn (DE)

(73) Assignee: Momentive Performance Materials GmbH, Leverkusen (DE)

( * ) Notice: Subject to any disclaimer, the term of this patent is extended or adjusted under 35 U.S.C. 154(b) by 944 days.

(21) Appl. No.: 10/552,558

(22) PCT Filed: Apr. 7, 2004

(86) PCT No.: PCT/EP2004/050472

§ 371 (c)(1),
(2), (4) Date: Dec. 14, 2006

(87) PCT Pub. No.: WO2004/090007

PCT Pub. Date: Oct. 21, 2004

(65) Prior Publication Data

US 2007/0106045 A1 May 10, 2007

(30) Foreign Application Priority Data

Apr. 11, 2003 (DE) ................. 103 16 662

(51) Int. Cl.
*D06M 15/643* (2006.01)
*C08G 77/26* (2006.01)

(52) U.S. Cl. .............. 528/28; 528/26; 528/38; 252/8.61; 252/8.63

(58) Field of Classification Search ................ 252/8.61, 252/8.63; 528/26, 28, 38
See application file for complete search history.

(56) References Cited

U.S. PATENT DOCUMENTS

| | | | | |
|---|---|---|---|---|
| 4,417,066 A | * | 11/1983 | Westall | 556/425 |
| 5,990,334 A | * | 11/1999 | Hierstetter et al. | 556/413 |
| 5,998,650 A | | 12/1999 | Schrock et al. | |
| 7,041,767 B2 | * | 5/2006 | Lange et al. | 528/28 |
| 2008/0194785 A1 | * | 8/2008 | Wagner et al. | 528/27 |
| 2008/0213208 A1 | * | 9/2008 | Moeller et al. | 424/78.03 |

FOREIGN PATENT DOCUMENTS

| | | |
|---|---|---|
| DE | 10003322 | 8/2001 |
| DE | 10036533 | 2/2002 |
| WO | WO02/10259 * | 2/2002 |

OTHER PUBLICATIONS

International Preliminary Report on Patentability for PCT/EP2004/050472 issued Mar. 2, 2006, six pages.

* cited by examiner

Primary Examiner—Marc S Zimmer
(74) Attorney, Agent, or Firm—Rankin, Hill & Clark LLP

(57) ABSTRACT

The invention relates to amino and/or ammonium-polysiloxane compounds comprising reactive, functional groups and salts of said compounds, especially polyquaternary polysiloxane copolymers and the salts therefrom. The invention also relates to methods for the production thereof, the use thereof for the surface treatment of substrates, such as natural or synthetic fibres or fibre-type substrates, especially as wash-resistant hydrophilic softeners. The invention further relates to the use thereof in cosmetic formulations, and formulations which contain reactive amino- and/or ammonium-polysiloxane compounds and the salts thereof.

21 Claims, No Drawings

REACTIVE AMINO-AND/OR AMMONIUM POLYSILOXANE COMPOUNDS

The invention relates to reactive, functionalized amino- and/or ammoniopolysiloxane compounds and salts thereof, in particular to polyquaternary polysiloxane copolymers and salts thereof, to processes for their preparation, to their use for surface treatment of substrates, such as natural or synthetic fibers or fiberlike substrates, in particular as wash-resistant hydrophilic softeners, and also to their use in cosmetic formulations, and to formulations which comprise the reactive amino- and/or ammonio polysiloxane compounds and their salts.

Amino-containing polysiloxanes are known as textile softeners (EP 441530).

The introduction of amino structures modified by ethylene oxide/propylene oxide units as side chains brings about an improvement in the hydrophilization effect (U.S. Pat. No. 5,591,880, U.S. Pat. No. 5,650,529). In this case, the alkylene oxide units allow the controlled adjustment of the hydrophilic-hydrophobic balance.

It has also been proposed to react $\alpha,\omega$-epoxy-modified siloxanes with $\alpha,\omega$-amino-functionalized alkylene oxides, and to use these products as hydrophilic softeners (U.S. Pat. No. 5,807,956, U.S. Pat. No. 5,981,681).

In a further development of this idea, block copolymers which are formed by reaction of $\alpha,\omega$-epoxy-modified siloxanes and $\alpha,\omega$-epoxy-functionalized alkylene oxides with primary amines have been described (U.S. Pat. No. 6,475,568). The primary amines serve as coupling groups between the two epoxy species.

To improve the substantivity, attempts have been undertaken to introduce quaternary ammonium groups into alkylene oxide-modified siloxanes.

The reaction of $\alpha,\omega$-diepoxides with tertiary amines in the presence of acids affords alkylene oxide-free $\alpha,\omega$-diquaternary siloxanes which can be used for haircare purposes (DE-C 3719086).

U.S. Pat. No. 6,242,554 describes $\alpha,\omega$-difunctional siloxane derivatives, each of which have a separate quaternary ammonium and alkylene oxide unit.

Strictly comblike alkylene oxide-modified polysiloxane quats have likewise been described (U.S. Pat. No. 5,098,979, U.S. Pat. No. 5,153,294, U.S. Pat. No. 5,166,297). The hydroxyl groups of comblike polyethersiloxanes, i.e. those substituted in the polysiloxane side chains, are converted with epichlorohydrin or chloroacetic acid to the corresponding halogen derivatives. Subsequently, quaternization is effected with tertiary amines.

The reaction of $\alpha,\omega$-diepoxysiloxanes with di-tertiary amines in the presence of acids affords alkylene oxide-free long-chain polyquaternary polysiloxanes (EP 282720). Analogous compounds based on $\alpha,\omega$-chloropropyl-substituted siloxanes are described in DE 3340708. Aromatic derivatives, preferably based on imidazole, are discussed in U.S. Pat. No. 6,240,929. The utilization of these polyquaternized aromatic structures is intended to improve the washout resistance from hair under the action of mild shampoos.

Linear siloxane copolymers which contain alkylene oxide and quat structures are claimed in DE 198 17 776.

However, none of the proposals discussed provides a satisfactory solution to the problem of obtaining the soft hand possible by virtue of silicones and the marked hydrophilicity after first finishing of a textile material even when it is exposed to the attack of aggressive detergent formulations in the course of repeated wash processes, possibly at elevated temperature.

Polyquaternized polysiloxanes are claimed in DE 100 51 258 as a softener for laundry detergents and in DE 100 36 533 additionally as softeners for initial textile finishing.

The documents WO 02/10256, WO 02/10257, WO 02/10259 of the Applicant discuss alkylene oxide-modified polyquaternized polysiloxanes as softeners in laundry detergents and for initial textile finishing. According to these patents, the hydrophilicity can be enhanced by controlled incorporation of units including alkylene oxide units, and an excellent softness and substantivity can at the same time be achieved.

The Applicant's documents DE 102 51 525.5 and DE 102 51 526.3, which were unpublished at the priority date of the present application, propose the establishment of a higher charge density by oligomerizing the quat structures between the silicone blocks, which has a positive effect on substantivity and hydrophilicity.

Crosslinked and/or branched structures have likewise been proposed. According to U.S. Pat. No. 6,177,511, crosslinking is effected by combination of aminosiloxanes with polyfunctional acrylic acid derivatives in a reaction analogous to a Michael addition. Quaternary ammonium groups may be introduced as acrylate derivatives.

Branched alkylene oxide-modified polysiloxane polyquats have been synthesized by condensation from $\alpha,\omega$-OH-terminated polysiloxanes and trialkoxysilanes. The quaternary ammonium structure is introduced via the trialkoxysilane, the quaternary nitrogen atom being substituted by alkylene oxide units (U.S. Pat. No. 5,602,224).

In a document of the Applicant which was yet to be published at the priority date of the present application (DE 102 12 470.1), controlled incorporation of trifunctional and higher-functionality amines or alkylene oxide-modified amines, or the incorporation of trifunctional and higher-functionality alkylating agents, for example based on epoxides or halocarboxylic esters, into the structures according to WO 02/10256, WO 02/10257, WO 02/10259 achieves branching/crosslinking which further enhances the level of properties regarding substantivity, softness and hydrophilicity.

Crosslinking siloxane systems are likewise known. According to DE 42 11 256, aminosiloxanes can be crosslinked in emulsion with silanes or siloxanes which have at least one carboxylic anhydride group. Stability of the formulation and particularly the hydrophilicity of the finishing are not sufficient. Alternatively, crosslinking can likewise be achieved by reaction with epichlorohydrin or diepoxides (WO 01/27232).

Self-crosslinking emulsions based on aminosiloxanes with terminal trialkoxysilyl structures which are part of the polyorganosiloxane skeleton are described in U.S. Pat. No. 4,661, 577 and US 2002 0028900. However, these structures contain only one polyorganosiloxane main chain and therefore do not allow any tailored configuration and adjustment of solubility, softness, hydrophilicity and substantivity. The molecular weight cannot be increased independently of the size of the polysiloxane main chain of any polyether side chain present.

Crosslinkable silicone quats are described in DE 32 36 466. The reaction of OH-terminated siloxanes with alkoxysilanes containing quaternary ammonium structures affords reactive intermediates which are substituted in a comblike manner and are said to crosslink alone or with suitable crosslinking agents, such as trialkoxysilanes, on the fiber surface to give wash-resistant layers.

None of the solutions proposed offers an answer to the question as to how the efficiency, especially the substantivity, of the polyquaternary polysiloxane compounds described as permanent hydrophilic softeners for textiles in WO 02/10256, WO 02/10257, WO 02/10259 in particular can be further significantly enhanced.

It is thus an object of the invention to describe highly efficient hydrophilic amino- and/or ammoniopolysiloxane compounds, in particular polyquatenary polysiloxane copolymer compounds (silicone quats), their preparation and use as wash-resistant hydrophilic softeners for initial textile finishing, the silicone quats imparting to the textiles, after appropriate application, a silicone-typical soft hand and marked hydrophilicity, and this property profile not being lost even after action of detergent formulations during repeated wash processes, possibly at elevated temperature. It is a further object of the invention to describe the use of these silicone quats as separate softeners after or as softeners in formulations based on nonionogenic or anionic/nonionogenic surfactants for washing of fibers and textiles, as an ironing aid, agents for preventing or reversing textile creasing, and also agents for finishing paper.

The object also applies to polysiloxane copolymers which are used in cosmetic formulations for skincare and haircare and whose substantivity can be improved in this way.

The fixing of surface-active polymers of the aforementioned structures to hard surfaces is likewise an object which has not been satisfactorily achieved and is achieved in this way.

It has been found that, surprisingly, the introduction of reactive groups which are stable in aqueous emulsions at 20° C. into amino- and/or ammoniopolysiloxane compounds, for example polyquaternary polysiloxane copolymers, as described, for example, in WO 02/10256, WO 02/10257, WO 02/10259, DE10036533, DE100 36 522, EP-A-282720, U.S. Pat. No. 6,240,929, DE 33 40 708 and the German patent applications DE 102 12 470.1, DE 102 51 525.5 and DE 102 51 526.3 which had not been published at the priority date of the present application, leads entirely surprisingly in the treatment of natural or synthetic fibers or fiberlike substrates (for example paper) to a distinctly enhanced permanence of the hydrophilicity with unchanged soft hand of the fibers.

The present invention thus provides:

Amino- and/or ammoniopolysiloxane compounds and salts thereof, characterized in that they have, as reactive groups, at least one functional group selected from groups of the formulae (I) and (II):

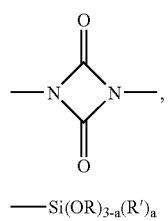

(I)

(II)

in which a is an integer from 0 to 2 and R and R' may be the same or different from one another and each represent an organic radical.

Amino- and/or ammoniopolysiloxane compound and salts thereof in the context of the invention are compounds which have at least one, preferably at least two, more preferably more than four, amino and/or ammonium groups and preferably at least one, more preferably at least two, even more preferably at least four, polyorganosiloxane blocks per molecule. The compounds mentioned preferably contain at least one, preferably at least two and more preferably at least four, quaternary ammonium groups per molecule. The compounds consist preferably of repeat units which contain the amino and/or ammonium groups mentioned and the polyorganosiloxane blocks mentioned.

The functional groups of the formula (I) and (II) mentioned are reactive groups which react upon activation, i.e. under the action of temperatures of appropriately at least 40° C., preferably 60° C., more preferably 80° C., even more preferably about 100° C., for example with condensation, rearrangement, addition reaction and/or reaction with a substrate, preferably with a fiber surface, or with crosslinking or reaction with themselves.

In the case of compounds with the groups of the formula (II), the activation of the reactive groups can be brought about in a preferred embodiment with addition of acids or bases as described below.

Reactive groups thus means here groups of the formula (I) or (II) in the inventive molecules which are capable, optionally with activation, of forming additional inter- or intramolecular bonds which increase the molecular weight, for example crosslinking, or make bonds to the substrate.

It is found that, surprisingly, the functional groups mentioned in the inventive amino- and/or ammoniopolysiloxane compounds and their salts are stable at 20° C. in aqueous emulsions, so that they are outstandingly suitable for use of the amino- and/or ammoniopolysiloxane compounds in aqueous emulsions. Thus, the reactive groups used in accordance with the invention exhibit a half-life in water at 20° C. of appropriately at least about 20 days, preferably at least about 30 days, more preferably at least about 40 days. The presence and the concentration of the reactive groups in the aqueous emulsions can be determined in a manner known per se, for example by IR and NMR spectroscopy methods. The reactivity of the functional or reactive groups can be increased by the presence of catalysts. Catalysts are acids or bases. The catalysts are used for activation preferably in the presence of the reactive groups of the formula (II) appropriately immediately before use, for example by addition of the catalysts to an aqueous mixture of the inventive compounds which comprises the fibrous substrates. Suitable acids include, for example, inorganic acid, for example hydrochloric acid, sulfuric acid, phosphoric acid, etc, or organic C1-C22-carboxylic acids. Suitable bases include, for example, inorganic bases such as alkali metal hydroxides, alkaline earth metal hydroxides, ammonia and organic bases, for example C1-C22-alkylamines.

In the functional group of the formula (II)

$$—Si(OR)_{3-a}(R')_a \qquad (II),$$

a is an integer from 0 to 2, and R and R' are the same or different from one another and are each an organic radical. "a" is 0, 1 or 2, preference being given to 0. R' is preferably selected from the group which consists of $C_1$ to $C_{22}$-alkyl, fluoro($C_3$-$C_{10}$)alkyl and $C_6$-$C_{10}$-aryl. R' is more preferably methyl. R is preferably selected from the group which consists of $C_1$ to $C_{22}$-alkyl, $C_5$ to $C_{10}$-cycloalkyl, $C_7$ to $C_{18}$-alkylaryl, $C_7$ to $C_{18}$-arylalkyl and $C_6$-$C_{10}$-aryl. R is preferably selected from secondary and tertiary alkyl groups or sterically demanding groups such as bis(tert-butyl)phenyl, cyclohexyl. R is more preferably isopropyl, sec-butyl, tert-butyl and sec-amyl.

The group of the formula (I) is sometimes referred to below as the uretdione group. The group of the formula (II) is sometimes referred to below as the alkoxysilyl group. The inventive compounds preferably contain only reactive groups of the formula (I) or only reactive groups of the formula (II). However, compounds which contain both reactive groups of the formula (I) and reactive groups of the formula (II) may also be encompassed by the invention. The preferred groups are selected depending on the application. The inventive compounds preferably contain the reactive group of the formula (I).

The inventive compounds are preferably those compounds which have at least three units, preferably at least 4, more preferably at least 6, units selected from the units Q and V, in which Q is at least one di-, tri- and/or tetravalent amino and/or ammomum group which is not bonded to V via a carbonyl carbon atom, and V is at least one organic unit which is bonded to the Q units via carbon, with the proviso that at least one of the units V contains a polyorganosiloxane radical. The inventive compounds preferably contain at least two, more preferably at least four, even more preferably at least six units V which contain a polyorganosiloxane radical. In a further preferred embodiment, the inventive compounds comprise at least two, preferably at least four, more preferably at least six, units Q.

The unit Q is selected from the group which consists of:

a saturated or unsaturated, diamino-functional heterocycle which is optionally substituted by further substituents and is of the formulae:

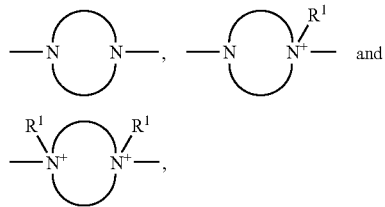

and also an aromatic, optionally substituted, diamino-functional heterocycle of the formula:

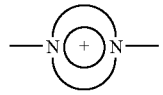

a trivalent radical of the formula:

a trivalent radical of the formula:

a tetravalent radical of the formula

in which $R^1$ is in each case hydrogen or a monovalent organic radical, which also permits the presence of silicon and in which, when a plurality of $R^1$ groups is present, they may be the same or different from one another. $R^1$ is preferably selected from $R^2$ radicals.

The units Q are not bonded to carbonyl carbon atoms of the V units. The inventive compounds preferably contain quaternary ammonium groups as Q units. Quaternary ammonium groups are positively charged nitrogen atoms which are bonded to four carbon atoms. The quaternary ammonium groups, which are described even more precisely below, are appropriately formed by alkylation with the aid of epoxides, haloalkyl compounds or the like. The alkylation to form the quaternary ammonium groups in the inventive compounds is effected generally with chain extension in the course of formation of oligomeric or polymeric inventive compounds using polyfunctional alkylating agents. However, it can also be effected after completion of formation of the oligomeric or polymeric skeleton of the inventive compounds with use of monofunctional alkylating agents. The inventive compounds preferably have at least two, more preferably at least four, even more preferably at least six, quaternary ammonium groups.

In a preferred embodiment of the invention, the unit V is selected from at least one polyvalent, straight-chain, cyclic or branched, saturated, unsaturated or aromatic hydrocarbon radical which has up to 1000 carbon atoms (where the carbon atoms of the optionally present polyorganosiloxane radical are not counted), may optionally contain one or more groups selected from

—O—,

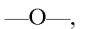

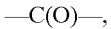

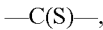

—$NR^2$— in which $R^2$ is hydrogen, a monovalent, straight-chain, cyclic or branched, saturated, unsaturated or aromatic hydrocarbon radical which has up to 300 carbon atoms, may contain one or more groups selected from —O—, —NH—, —C(O)— and —C(S)—, and may optionally be substituted by one or more substituents selected from the group which consists of a hydroxyl group, an optionally substituted heterocyclic group which preferably contains one or more nitrogen atoms, polyether radicals, polyetherester radicals, polyorganosiloxanyl radicals and —$Si(OR)_{3-a}(R')_a$, in which a, R and R' are each as defined above, where, when a plurality of —$NR^2$— groups are present, they may be the same or different, and with the proviso that the —$NR^2$— group bonds to a carbonyl and/or thiocarbonyl carbon atom, may contain

and
polyorganosiloxane radicals, and may optionally be substituted by one or more hydroxyl groups and/or groups of the formula (II)

in which a, R and R' are each as defined above, and with the proviso that at least one V radical contains at least one polyorganosiloxane radical, and in which the polyvalent Q and V groups bonded to one another are saturated terminally by monovalent organic radicals. The V group contains in particular the units the units U defined below.

The naming of the group of the formula (II) both as a substituent of the $R^2$ group and of the V group means that the group mentioned is either bonded to the main chain via amide nitrogen part of a terminal $R^2$ group or may be bonded in the V or Q groups to the main chain via a carbon atom via an aliphatic group.

In the units V mentioned, the polyorganosiloxane radical mentioned is appropriately a divalent group of the formula (III):

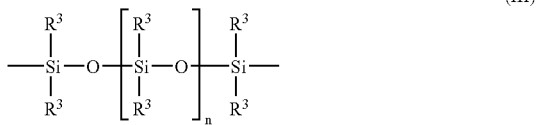

in which $R^3$ may be the same or different and is selected from the group which consists of $C_1$ to $C_{22}$-alkyl, fluoro($C_3$-$C_{10}$) alkyl, $C_6$-$C_{10}$-aryl and —W—Si(OR)$_{3-a}$(R')$_a$ in which R, R' and a are each as defined above and W is —O— or a divalent, straight-chain, cyclic or branched, saturated, unsaturated or aromatic hydrocarbon radical which has up to 100 carbon atoms and may contain one or more —C(O)—, —O—, —NH—, —S— groups, and may optionally be substituted by hydroxyl groups, and n=from 0 to 1000. The inventive amino- and/or ammoniopolysiloxane compounds and salts thereof appropriately contain an average of at least one, preferably at least two, more preferably more than three, of the units V mentioned, which contain a polyorganosiloxane radical of the formula (III).

More preferably, the inventive compounds which have the functional group of the formula (II) but no functional group of the formula (I) contain at least three units V which have a polyorganosiloxane radical of the formula (III). These compounds accordingly have at least two Q groups which lie between the units V.

When the inventive compounds have a functional group of the formula (I), they contain at least one, preferably two, more preferably at least three, units V which have a polyorganosiloxane radical of the formula (III).

"n" in the polyorganosiloxane radical of the formula (III) is preferably from 20 to 200. The polyorganosiloxane radicals in the units V may be the same or different from one another.

The inventive compounds contain preferably at least one unit, more preferably at least two units, of the formula (IV):

where Q and V are each as defined above, and the Q and V groups are saturated terminally by monovalent organic groups.

The inventive amino- and/or ammoniopolysiloxane compounds and salts thereof may, for example, be polyamino- and/or polyammoniopolysiloxane compounds. The polyamino- and/or polyammoniopolysiloxane compounds are appropriately copolymer compounds which have amino and/or ammonium repeat units and polysiloxane repeat units in the main polymer chain. The amino units appropriately contain secondary and/or tertiary nitrogen atoms (2 or 3 organic radicals on the uncharged nitrogen atom). The ammonium units contain secondary, tertiary and/or quaternary, positively charged nitrogen atoms (2, 3 or 4 organic radicals on the nitrogen). The amino and/or ammonium repeat units used may also be heterocyclic radicals bonded into the polymer chain via two nitrogen atoms.

The inventive amino- and/or ammoniopolysiloxane compounds and salts thereof may also be amino- and/or ammoniopolysiloxane compounds which, in the pendant groups of a polyorganosiloxane group, contain amino and/or ammonium groups which preferably bond to further polyorganosiloxane groups. In other words, the amino and/or ammonium groups are not disclosed in the main chain composed of polyorganosiloxane repeat units.

The difference can be illustrated as follows:

Polyamino- and/or polyammoniopolysiloxane compound with (α,ω-bonded siloxane-containing V groups:

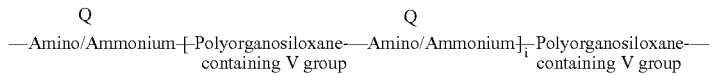

Amino- and/or ammoniopolysiloxane compound:
(P1) type

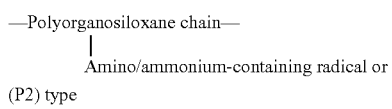

(P2) type

-continued

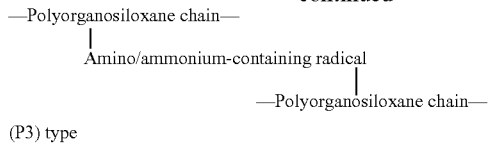

(P3) type

In the inventive polyamino- and/or polyammonmopolysiloxane compound, which preferably contain at least two units of the formula (IV):

-[Q-V]-     (IV)

in which Q and V are each as defined above, and the V and Q groups are saturated terminally by monovalent organic groups, the units V are, for example, selected from the group which consists of $V^1$, $V^2$ and $V^3$, $V^2$ is a divalent V group which is as defined above, and $V^2$ contains at least one long-chain polysiloxane radical —$Z^2$— of the formula (V)

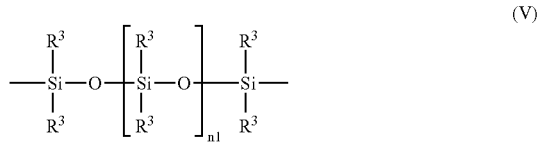
(V)

in which $R^3$ is as defined above and $n_1$=from 20 to 1000.

$V^1$ is a divalent V group which is as defined above, does not contain a long-chain polysiloxane radical —$Z^2$— of the formula (V) and may optionally contain a short-chain polysiloxane radical —$Z^1$— of the formula (VI)

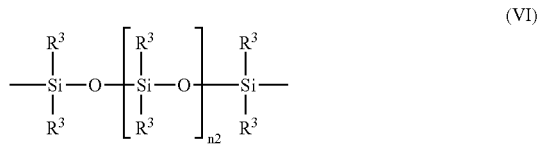
(VI)

in which $R^3$ is as defined above and $n_2$=from 0 to 19.

$V^3$ is a trivalent or higher-valency V group which is as defined above, and $V^3$ contains at least one trivalent or higher-valency organopolysiloxane unit.

The inventive polyamino- and/or polyammoniopolysiloxane compounds, which contain at least one unit, more preferably at least two units, of the formula (IV):

-[Q-V]-     (IV)

are appropriately terminated by monofunctional -Q-$R^4$ and/or —V—$R^4$ groups as the end group, in which $R^4$ is a monovalent organic radical, preferably methyl, hydrogen or hydroxyl.

In a preferred embodiment, the —V—$R^4$ group may also be a siloxane group which is not bonded via an $R^3{}_2$SiO group to $V^{2*}$ or the remaining V (P1) type, but rather bonded to $V^{2*}$ or V via only one $R^3$SiO unit, i.e. a side group ((P2) and (P3) type).

This copolymer accordingly preferably has 2 units of the formula (IIIb) as the end group which border the repeat units V and Q, where V and Q have the compositions mentioned.

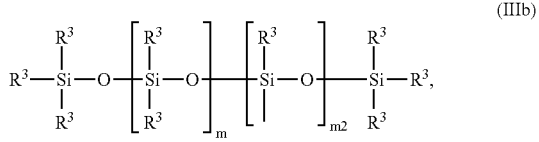
(IIIb)

in which $R^3$, m and $m_2$ are each as defined above.

The inventive polyamino- and/or polyammoniopolysiloxanes which contain at least one unit of the formula (IV) are also intended to include the case in which only one unit -[Q-V]— is present, so that compounds of the formulae $R^4$—V-[Q-V]—$R^4$ and $R^4$—V-[Q-V]-Q-$R^4$ can also be included. Preference is then given to polydialkylsiloxane-terminated copolymers in which a divalent unit V between two Q units contains at least one uretdione-containing unit.

Examples of such polymers but without uretdione-containing structural units can be found in WO 02/10256.

These amino- and/or ammoniopolysiloxane compounds with 2 units of the formula (IIIb) which bond to independent V2* radicals are structures of the P1 and P2 type.

The inventive polyamino- and/or polyammoniopolysiloxanes which contain at least unit of the formula (IV) are, for example, linear polysiloxane copolymers of the general formula (IV'):

-[Q-V]—     (IV')

in which Q is as defined above, V is at least one $V^1$ group and/or at least one $V^2$ group, in which $V^1$ and $V^2$ are each as defined above.

In the general formulae (IV) and (IV'), the molar ratio of the groups $V^1$ and $V^2$ in the polysiloxane compounds $V^2/V^1$ may in principle assume any value. The invention thus also includes the case in which the polysiloxane compound of the formula (IV) or (IV') contains only $V^2$ units, i.e. the polysiloxane compound has the formula -[Q-$V^2$]—. The invention also includes the case in which the polysiloxane compound contains only $V^1$ units. In this case, the $V^1$ units, however, have to contain $Z^1$ siloxane units.

In a preferred embodiment of the invention, the polysiloxane compound of the formulae (IV) or (IV'), however, contains both $V^2$ and $V^1$ units.

The molar ratio of the $V^1$ and $V^2$ groups in the polysiloxane compounds of the general formulae (IV) and (IV') may be adjusted depending on the desired objectives, such as softness, hydrophilicity and substantivity, of the inventive compounds. In a preferred embodiment of the invention, the ratio of the $V^1$ to $V^2$ groups is about 1:1, $V^1$ in a particularly preferred embodiment not containing any polysiloxane $Z^1$ and, at the same time, two different $V^1$ radicals, for example hexamethylene and bis-alkyl-terminated polyether, being present, as shown in Example 3. The structure of such linear polyamino- or polytetraorganoammonium compounds has been described, for example, in WO 02/10257, WO 02/10259, EP 282720 or U.S. Pat. No. 5,981,681. Particular preference is given to the poiyamino- or polyammoniopolysiloxane skeletons of WO 02/10259 and of WO 02/10257, whose polysiloxane polymers defined in claim 1 are hereby explicitly incorporated by reference and are included in the disclosure content of the present application. In a further embodiment of the linear polyamino- or polyammoniopolysiloxane compounds of the formula (IV) or (IV'), $V^2/V^1$ is unequal to 1; $V^2/V^1$ is preferably <1, more preferably <0.9; even more preferably, $V^2/V^1$ satisfies the relationship $0.005 < V^2/V^1 < 0.5$.

The $R^4$ group is preferably selected from the $R^2$ groups.

In a preferred embodiment of the invention, the divalent Q radical in the formulae (IV) or (IV') is selected from the group which consists of:

a quaternized imidazole unit of the structure

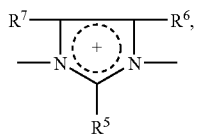

a quaternized pyrazole unit of the structure

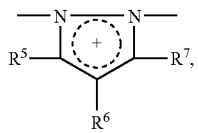

a diquaternized piperazine unit of the structure

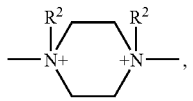

a monoquaternized piperazine unit of the structure

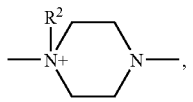

a monoquaternized piperazine unit of the structure

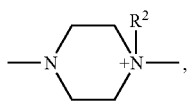

a diquaternized unit of the structure

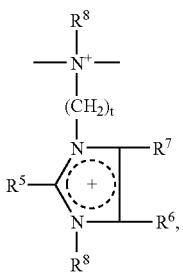

a monoquaternized unit of the structure

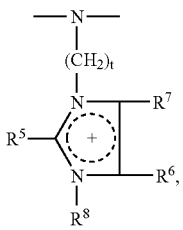

a monoquaternized unit of the structure

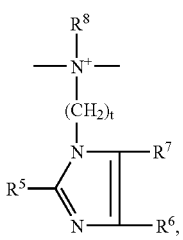

a diquaternized unit of the structure

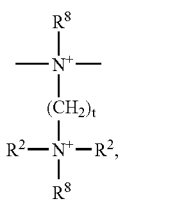

a monoquaternized unit of the structure

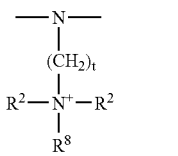

and a monoquaternized unit of the structure

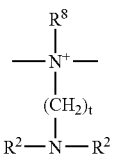

in which t is from 2 to 10, $R^2$ is as defined above, and when a plurality of $R^2$ radicals are present, they may be the same or different, and two $R^2$ radicals together with the nitrogen atom form a five- to seven-membered heterocycle which may optionally additionally have one or more nitrogen, oxygen and/or sulfur atoms.

$R^5$, $R^6$, $R^7$ may be the same or different and are selected from the group which consists of: hydrogen, halogen, hydroxyl group, nitro group, cyano group, thiol group, carboxyl group, alkyl group, monohydroxyalkyl group, polyhydroxyalkyl group, thioalkyl group, cyanoalkyl group, alkoxy group, acyl group, acetyloxy group, cycloalkyl group, aryl group, alkylaryl group, and groups of the —$NHR^w$ type in which $R^w$ is H, alkyl group, monohydroxyalkyl group, polyhydroxyalkyl group, acetyl group, ureido group, and in each case two of the adjacent $R^5$, $R^6$ and $R^7$ radicals with the carbon atoms bonding them to the heterocycle may form aromatic five- to seven-membered rings, and $R^8$ is as defined for $R^2$, where $R^8$ and $R^2$ may be the same or different.

In a preferred embodiment of the polysiloxane compounds of the formula (IV) or (IV') as component b1), $V^2$ is a group of the formula

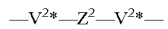

in which $Z^2$ is as defined above and $V^{2*}$ is a divalent straight-chain, cyclic or branched, saturated, unsaturated or aromatic hydrocarbon radical which has up to 40 carbon atoms and may optionally contain one or more groups selected from —O—, —CONH—, —$CONR^2$— in which $R^2$ is as defined above, —C(O)— and —C(S)—, and the $V^{2*}$ radical may optionally be substituted by one or more hydroxyl groups.

In the abovementioned embodiment, the inventive linear polysiloxane copolymer may have the following repeat units:

—[$V^{2*}$—$Z^2$—$V^{2*}$-Q]-, preferably together with
—[$V^1$-Q]-.

The molar ratio of the repeat units —[$V^{2*}$—$Z^2$—$V^{2*}$-Q]- to —[$V^1$-Q]-, i.e. the $V^2/V^1$ ratio, may, as mentioned above, be adjusted suitably and, for example, be 1, but is, in a preferred embodiment, preferably unequal to 1, more preferably <0.5. In the later case, the linear polyamino- or polyammoniopolysiloxane copolymers -[Q-V]— mentioned necessarily contain blocks which contain more than one —[$V^1$-Q]- unit bonded to one another.

As will be explained in detail below in connection with the process for preparing the above-described linear polysiloxane copolymers, the blocklike sequences which have more than one —[$V^1$-Q]- unit bonded to one another, depending on the preparation method, may be bonded regularly to the $V^2$-Q units or irregularly to the $V^2$-Q units.

This means the following:

In the case of the regular bonding, in which, for example, a prepolymer corresponding to the -Q-[$V^1$-Q]$_x$— group is reacted with monomer units corresponding to $V^2$ in a molar ratio of 1:1, the linear polysiloxane copolymers can be represented as follows:

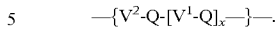

x may be from 2 to 2000 and is the mean value of the distribution. The linear polysiloxane copolymers illustrated by the formula —{$V^2$-Q-[$V^1$-Q]$_x$—}- are characterized in that they have substantially no —$V^2$-Q- units bonded to one another, or, in other words, two —$V^2$-Q- units are always interrupted by at least one —$V^1$-Q- unit.

In the case of the irregular bonding, in which, for example, monomers corresponding to Q units are reacted with monomer units corresponding to $V^1$ and monomer units corresponding to $V^2$ in a ratio of Q/($V^1$+$V^2$), with, for example, $V^2N^1$<1, preferably <0.5, of 1:1, the linear polysiloxane copolymers can be represented as follows:

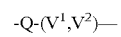

in which V the ratio $V^2/V^1$ is <1 or <0.5. In this case, the $V^1$ and $V^2$ groups are distributed randomly over the copolymer chain. In contrast to the linear polysiloxane copolymers prepared by the regular bonding, this copolymer may also have adjacent -Q-$V^2$— units.

In a preferred embodiment of the polysiloxane compound of the formula (IV) or (IV') used in accordance with the invention, the $V^1$ group is selected from divalent, straight-chain, cyclic or branched, saturated, unsaturated or aromatic hydrocarbon radicals which have up to 400 carbon atoms and may optionally contain one or more groups selected from —O—, —CONH—, —$CONR^2$— in which $R^2$ is as defined above, —C(O)—, —C(S)— and —$Z^1$— in which —$Z^1$— is a group of the formula

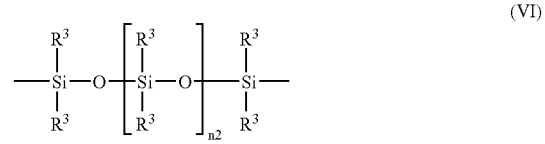

(VI)

in which $R^3$ is preferably $C_1$-$C_{18}$-alkyl which may optionally be substituted by one or more fluorine atoms, or phenyl, and $n_2$ is as defined above.

In a further preferred embodiment of the polysiloxane compounds of the formula (IV) or (IV'), the Q group is selected from:

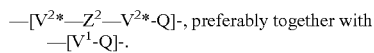

a quaternized imidazole unit of the structure

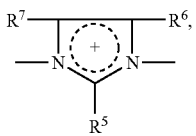

a quaternized pyrazole unit of the structure

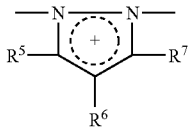

a diquaternized piperazine unit of the structure

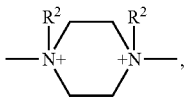

a monoquaternized piperazine unit of the structure

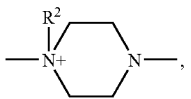

a monoquaternized piperazine unit of the structure

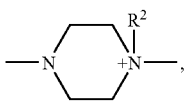

a monoquaternized unit of the structure

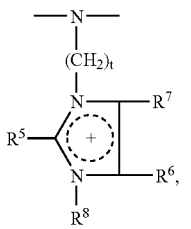

in which $R^2$, $R^4$, $R^5$, $R^6$, $R^7$ and $R^8$ are each as defined above.

In a further preferred embodiment of the linear polysiloxane compounds of the formula (IV') as the present invention, the molar $V^2/V^1$ ratio satisfies the relationship $$0.0005 < V^2/V^1 < 0.5, (=2V^1/V^2 < 2000)$$

more preferably the relationship $$0.005 < V^2/V^1 < 0.5, (=2.5 < V^1/V^2 < 200)$$

even more preferably the relationship $$0.01 < V^2/V^1 < 0.5, (=3.3 < V^1/V^2 < 100).$$

Preferably, in the formulae (IV) and (IV'):

$R^3 = C_1$ to $C_{18}$ alkyl, in particular methyl, ethyl, trifluoropropyl and phenyl, $n_1$ = from 20 to 400, more preferably from 20 to 300, especially from 20 to 200. In a further preferred embodiment, $n_1$ is between 20 and 50 or between 80 and 200. The number $n_1$ is the mean degree of polymerization from $M_n$ of the diorganosiloxy units in the $Z^2$ group.

$n_2$ = from 0 to 15, more preferably from 0 to 10, especially from 0 to 5, more especially 0. The number $n_2$ is the mean degree of polymerization from $M_n$ of the diorganosiloxy units in the $Z^2$ group.

$V^{2*}$ = a divalent straight-chain, cyclic or branched, saturated, unsaturated $C_3$ to $C_{16}$ hydrocarbon radical or aromatic $C_8$ to $C_{20}$ hydrocarbon radical which may optionally contain one or more groups selected from —O—, CONH—, —CONR²—, —C(O)—, —C(S)— and may be substituted by one or more OH groups, in which $R^2$ is as defined above.

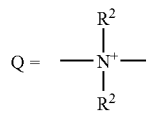

a quaternized imidazole unit of the structure

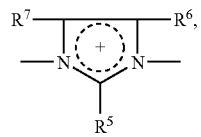

a diquaternized piperazine unit of the structure

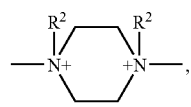

a monoquaternized piperazine unit of the structure

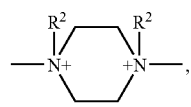

a monoquaternized piperazine unit of the structure

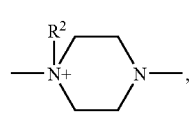

a monoquaternized piperazine unit of the structure

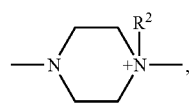

a monoquaternized unit of the structure

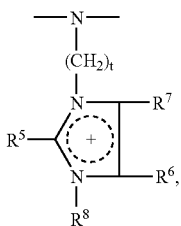

in which $R^2$, $R^4$, $R^5$, $R^6$, $R^7$ and $R^8$ are each as defined above.

More preferably, $V^{2*}$ is a divalent straight-chain, cyclic or branched, saturated, unsaturated or aromatic hydrocarbon radical which has up to 16 carbon atoms and may contain one or more groups selected from —O—, —CONH—, —CONR$^2$— in which $R^2$ is as defined above, —C(O)—, —C(S)—, and may be substituted by one or more hydroxyl groups. Even more preferably, —$V^{2*}$— is selected from groups of the formulae:

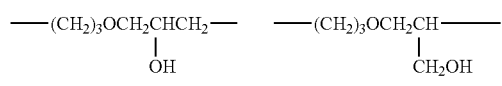

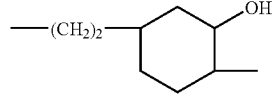

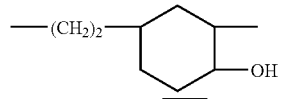

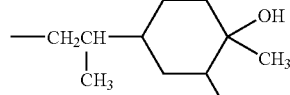

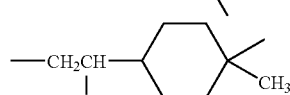

—(CH$_2$)$_2$—, —(CH$_2$)$_3$—, —(CH$_2$)$_4$—,

—(CH$_2$)$_5$—, —(CH$_2$)$_6$—, —CH=CHCH$_2$—,

—CH=CHCH$_2$CH$_2$—, —CH$_2$CH$_2$CH$_2$OC(O)CH$_2$—,

—CH$_2$CH$_2$CH$_2$OC(O)CH$_2$CH$_2$—,

—CH=CH$_2$CH$_2$OC(O)CH$_2$—,

—CH=CH$_2$CH$_2$OC(O)CH$_2$CH$_2$—

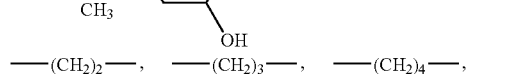

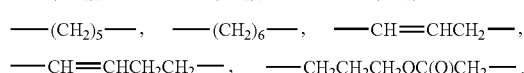

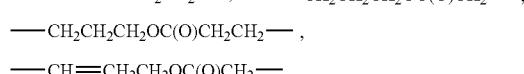

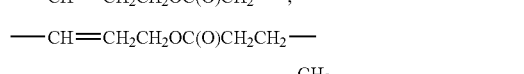

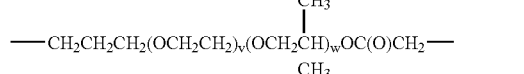

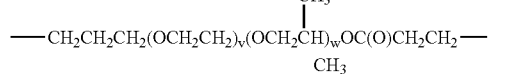

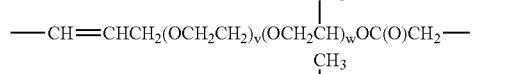

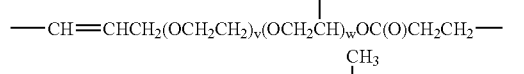

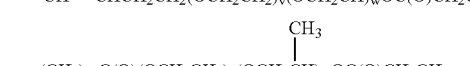

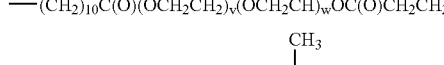

where $v + w \geq 0$,

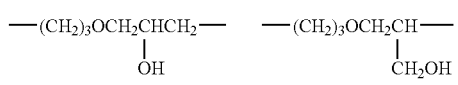

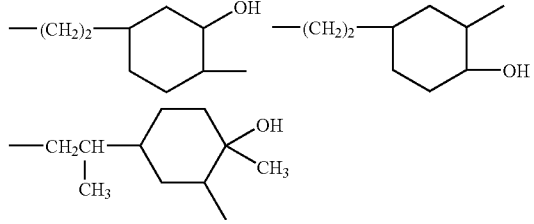

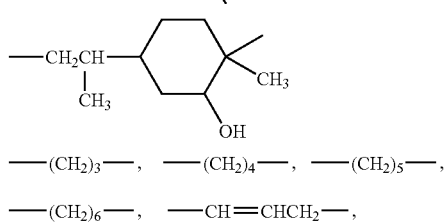

—(CH$_2$)$_3$—, —(CH$_2$)$_4$—, —(CH$_2$)$_5$—,

—(CH$_2$)$_6$—, —CH=CHCH$_2$—,

—CH=CHCH$_2$—, —CH=CHCH$_2$CH$_2$—,

—CH$_2$CH$_2$CH$_2$OC(O)CH$_2$—,

—CH$_2$CH$_2$CH$_2$OC(O)CH$_2$CH$_2$—, $R^2$ is preferably: H, —CH$_3$, —CH$_2$CH$_3$, —(CH$_2$)$_2$CH$_3$,

—(CH$_2$)$_3$CH$_3$, —(CH$_2$)$_5$CH$_3$, —CH$_2$CH$_2$OH,

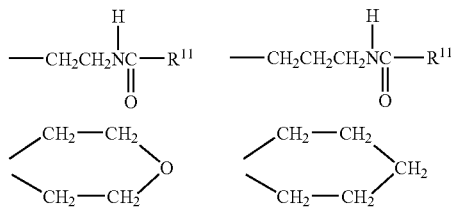

where $R^{11}$=straight-chain, cyclic or branched C$_1$ to C$_{18}$ hydrocarbon radical which may contain one or more groups selected from —O—, —NH—, —C(O)— and —C(S)— and may be substituted by one or more OH groups, especially unsubstituted C$_5$ to C$_{17}$ hydrocarbon radicals which derive from the corresponding fatty acids or else hydroxylated C$_3$ to C$_{17}$ radicals which can be traced back to hydroxylated carboxylic acids, especially saccharide carboxylic acids, and quite especially

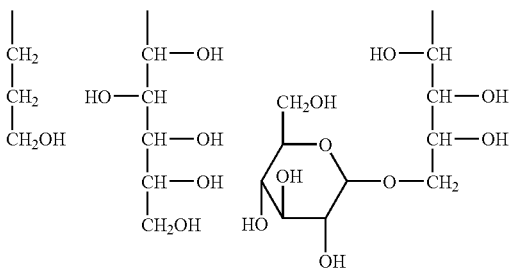

In addition, $R^2$ is preferably:

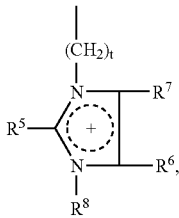

in which t, $R^5$ to $R^8$ are each as defined above,

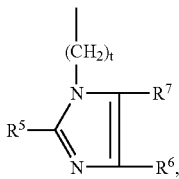

in which t, $R^5$ to $R^7$ are each as defined above,

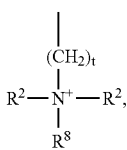

in which t, $R^2$ and $R^8$ are each as defined above.

$V^1$ is preferably
- $—R^9—$ in which $R^9$ is a divalent, saturated or mono- or polyunsaturated, straight-chain or branched hydrocarbon radical having from two to 25 carbon atoms,
- $—(CH_2)_uC(O)O—[(CH_2CH_2O)_q—(CH_2CH(CH_3)O)_r]—C(O)(CH_2)_u—$
- $—(CH_2)_uC(O)O—R^9—O—C(O)(CH_2)_u—$, in which $R^9$ is as defined above,
- $—(CH_2)_uR^{10}—(CH_2)_u$, in which $R^{10}$ is an aromatic group,
- $—[CH_2CH_2O]_q—[CH_2CH(CH_3)O]_r—CH_2CH_2—$,
- $—CH(CH_3)CH_2O[CH_2CH_2O]_q—[CH_2CH(CH_3)O]_r—CH_2CH(CH_3)—$
- $—CH_2CH(OH)CH_2—$,
- $—CH_2CH(OH)(CH_2)_2CH(OH)CH_2—$,
- $—CH_2CH(OH)CH_2OCH_2CH(OH)CH_2OCH_2CH(OH)CH_2—$ and
- $—CH_2CH(OH)CH_2O—[CH_2CH_2O]_q—[CH_2CH(CH_3)O]_r—CH_2CH(OH)CH_2—$ in which u is from 1 to 3, q and r are each from 0 to 200, preferably from 0 to 100, more preferably from 0 to 70 and particularly preferably from 0 to 40, and q+r>0.

Preferred variants of $V^1$ are structures of the formula:

- $—CH_2C(O)O—[CH_2CH_2O]_q—[CH_2CH(CH_3)O]_r—C(O)CH_2—$,
- $—CH_2CH_2C(O)O—[CH_2CH_2O]_q—[CH_2CH(CH_3)O]_r—C(O)CH_2CH_2—$,
- $—CH_2CH_2CH_2C(O)O—[CH_2CH_2O]_q—[CH_2CH(CH_3)O]_r—C(O)CH_2CH_2CH_2—$, esterified alkylene, alkenylene, alkynylene units, especially of the structures
- $—CH_2C(O)O—[CH_2]_o—OC(O)CH_2—$,
- $—CH_2CH_2C(O)O—[CH_2]_o—OC(O)CH_2CH_2—$,
- $—CH_2CH_2CH_2C(O)O—[CH_2]_o—OC(O)CH_2CH_2CH_2—$,
- $—CH_2C(O)O—CH_2C≡CCH_2—OC(O)CH_2—$,
- $—CH_2CH_2C(O)O—CH_2C≡CCH_2—OC(O)CH_2CH_2—$,
- $—CH_2CH_2CH_2C(O)O—CH_2C≡CCH_2—OC(O)CH_2CH_2CH_2—$,
- $—CH_2C(O)O—CH_2CH=CHCH_2—OC(O)CH_2—$,
- $—CH_2CH_2C(O)O—CH_2CH=CHCH_2—OC(O)CH_2CH_2—$,
- $—CH_2CH_2CH_2C(O)O—CH_2CH=CHCH_2—OC(O)CH_2CH_2CH_2—$, alkylene, alkenylene, alkynylene and aryl units, especially of the structures:
- $—[CH_2]_o—$ where o=from 2 to 6, $—CH_2C≡CCH_2—$, $—CH_2CH=CHCH_2—$, $—CH(CH_3)CH_2CH_2—$,

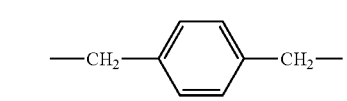

polyalkylene oxide units, especially of the structures

- $—[CH_2CH_2O]_q—[CH_2CH(CH_3)O]_r—CH_2CH_2—$,
- $—CH(CH_3)CH_2O[CH_2CH_2O]_q—[CH_2CH(CH_3)O]_r—CH_2CH(CH_3)—$ where mono-, di- or polyhydroxy-functional units, especially of the structures

- $—CH_2CH(OH)CH_2—$, $—CH_2CH(OH)(CH_2)_2CH(OH)CH_2—$,
- $—CH_2CH(OH)CH_2OCH_2CH(OH)CH_2OCH_2CH(OH)CH_2—$,
- $—CH_2CH(OH)CH_2O—[CH_2CH_2O]_q—[CH_2CH(CH_3)O]_r—CH_2CH(OH)CH_2—$ where
q=from 0 to 200,
r=from 0 to 200.
Preferably, q=from 1 to 50, in particular from 2 to 50, especially from 1 to 20, very especially from 1 to 10, and also 1 or 2, r=from 0 to 100, in particular from 0 to 50, especially from 0 to 20, very especially from 0 to 10, and also 0 or 1 or 2.
The branch unit $V^3$ may be silicone-free. Examples thereof include:
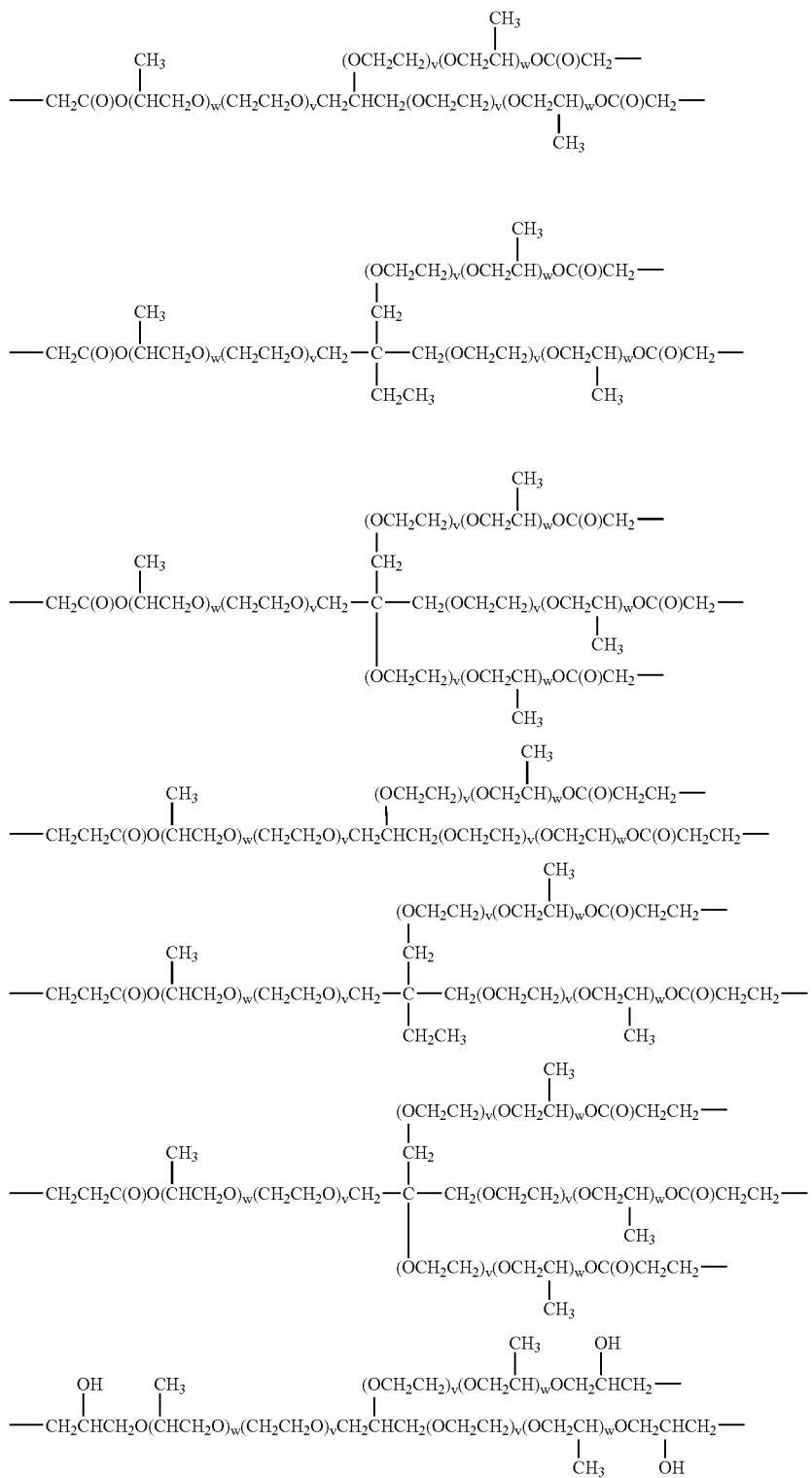

-continued
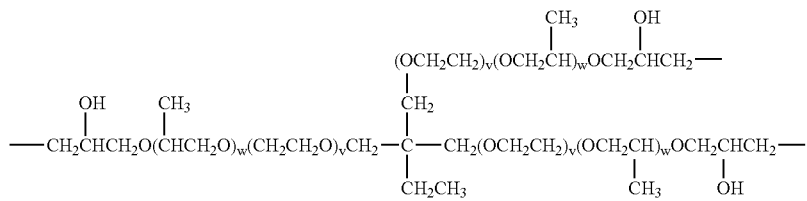
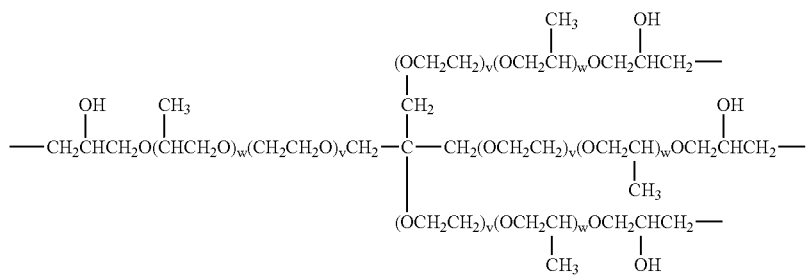
where v + w ≥ 0.
The branch unit $V^3$ may contain a trivalent or higher-valency organopolysiloxane unit, for example:
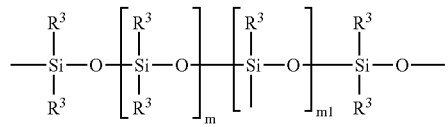
(VIIa)
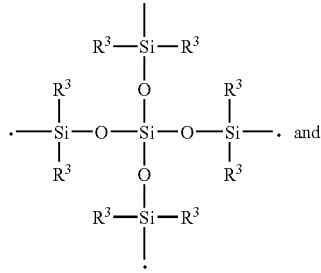
(VIIc)
and
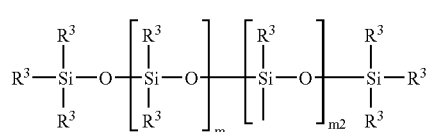
(VIIb)
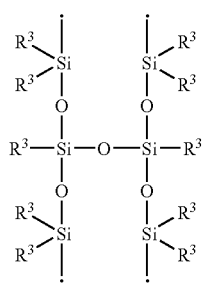
(VIId)
in which $R^3$ is as defined above, m=from 0 to 1000, and $m^1 \geq 1$ and $m^2 \geq 3$,
in which $R^3$ is in each case as defined above.

An example of a $Z^3$-containing branch unit $V^3$ is, for example:

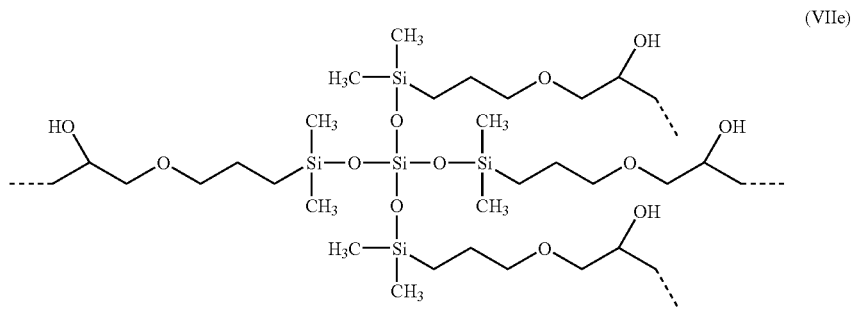

(VIIe)

The inventive amino- and/or ammoniopolysiloxane compound can be prepared appropriately by a process in which a) at least one amine compound selected from a diamine compound and/or a primary or secondary monoamine compound is reacted with a multifunctional, preferably difunctional, organic compound capable of reaction with the amino functions of the amine compound, the molar ratio of the amino functions of the amine compound mentioned to the functional groups of the multi functional, preferably difunctional, organic compound mentioned being from about 0.5 to 2, or b) at least two moles of an amine compound (1) selected from a diamine compound (1) and/or a primary or secondary monoamine compound (1) is reacted with one mole of a multifunctional, preferably difunctional, organic compound (1) capable of reaction with the amino functions of the amine compound to form a diamine compound (2) (monomer), and the diamine compound (2) (monomer) is subsequently reacted with at least one further multifunctional, preferably difunctional, organic compound (2) capable of reaction with the amino functions of the diamine compound (2), optionally in the presence of further amine compounds (2), the stoichiometry of the amino functions and the functional groups capable of reaction with amino functions in the last stage of the reaction being about 1:1, and the organic compounds (1) and (2) being the same or different from one another, or c) an amine compound selected from a diamine compound (1) and/or a primary or secondary monoamine compound is reacted with a multifunctional, preferably difunctional, organic compound (1) capable of reaction with the amino functions of the amine compounds to form a diamine compound (2) (amino-terminated oligomer), the molar ratio of the amino functions of the amine compound mentioned to the functional groups of the multifunctional, preferably difunctional, organic compound (1) mentioned being from about 1 to 2, then the resulting diamine compound (2) (amino-terminated oligomer) is reacted with at least one multifunctional, preferably difunctional, organic compound (2) capable of reaction with the amino functions of the diaamine compounds, the stoichiometry of the amino functions and of the functional groups capable of reaction with amino functions in the last stage of the reaction being about 1:1, and the organic compounds (1) and (2) being the same or different, or d) an amine compound (1) selected from a diamine compound and/or a primary or secondary monoamine compound is reacted with a multifunctional, preferably difunctional, organic compound (1) capable of reaction with the amino functions of the amine compound to form a multifunctional, preferably difunctional, organic compound (2) (difunctional oligomer) capable of reaction with amino functions, the molar ratio of the amino functions of the amine compound mentioned to the functional groups of the multifunctional, preferably difunctional, organic compound (1) mentioned being from about 0.5 to 1, then the organic compound (2) (difunctional oligomer) is reacted with at least one amine compound (2) selected from a diamine compound and/or a primary or secondary monoamine compound, optionally in the presence of one or more multifunctional, preferably difunctional, organic compounds (3) capable of reaction with amino functions, the stoichiometry of the amino functions and the functional groups capable of reaction with amino functions in the last stage of the reaction being about 1:1, in the course of which, if appropriate, monofunctional, preferably tertiary, monoamines or suitable monoamines incapable of chain propagation and/or monofunctional compounds capable of reaction with amino functions may be added as chain terminators, and in the course of which any amino functions present in the resulting products may subsequently be protonated or quaternized.

Based on the compounds of the formula (IV) with the units Q and V, the process variants mentioned can be illustrated, for example, as follows:

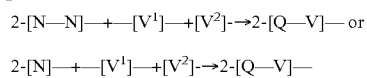

where —[N—N]— is a diamine which may also include a $V^1$-containing diamine —[N—V$^1$—N]— or a $V^2$-containing diamine —[N—V$^{2*}$—Z$^{2*}$—V$^{2*}$—N]—, and —[V$^1$]— and —[V$^2$]— are intended to represent monomers corresponding to the repeat units $V^1$ and $V^2$, and —[N]— represents a primary or secondary monoamine suitable for chain propagation.

The —[N—N]— and/or —[N]-units form at least one quaternary ammonium unit Q, the quaternization, depending on the type of bond between —[N—N]— or —[N]— units and —[V]— units, optionally also being effected after the polymerization in a separate step.

Preferred examples of —[N—N]— are, as described in detail below, piperazine, imidazole; preferred diamine units —[N—$V^1$—N]— include, for example: polymethylenediamines such as hexamethylenediamine, ($\alpha,\omega$-diamino-terminated polyethers, for example Jeffamine, etc.

Preferred diamine units —[N—$V^{2*}$—$Z^2$—$V^{2*}$—N]— include, for exaple reaction products of $\alpha,\omega$-dihydropolydialkylsiloxanes with allylamines.

Preferred examples of —[N]— are as described in detail below, for example dimethylamine.

The use of diamines —[N—N]— is preferred per se.

Preferred —[V]— monomers include, for example, epichlorohydrin, bisepoxides, biscarbonyl chlorides, diisocyanates or bisacrylates. It is preferably also possible to react mixtures of the —[$V^1$]— monomers mentioned, for example mixtures of epichlorohydrin, bischloroalkyl esters or bisepoxides.

Preferred —[$V^2$]— monomers are monomers of the formula —[$V^{2*}$—$Z^2$—$V^{2*}$]— in which $Z^2$ is as defined above, and —[$V^{2*}$]— represents a functionalized group corresponding to the repeat unit $V^{2*}$. Preferred —[$V^2$]— monomers for forming the $V^2$ repeat units are in particular $\alpha,\omega$-diepoxy-terminated polydialkylsiloxanes.

A further variant which can be carried out both with diamines, —[N—N]—, and suitable monoamines —[N]— is defined as follows:

Step 1): 2-[N—N]—+—[$V^2$]— or —[$V^1$]—⌴—[N—N—$V^1$—N—N]— or [N—N—$V^2$—N—N]—

Step 2.1): —[N—N—$V^2$—N—N]—+—[$V^1$]—+—[$V^1$]—+—[N—N]—→Q$V^2$Q$V^1$Q or Q$V$Q$V^2$Q$V$Q$V^1$Q$V$Q, Step 2.2): —[N—N—$V^1$—N—N]—+—[$V^2$]—+—[N—N]—→Q$V^1$Q$V^2$Q or Q$V$Q$V^1$Q$V$Q$V^2$Q$V$Q With regard to the monomer units —[N—N]—, —[$V^1$]— and —[$V^2$]— used with preference, the above statements apply.

A further variant is as follows:

Step 1): 2-[N]—+—[$V^2$]— or —[$V^1$]—→—[N—$V^1$—N]— or —[N—$V^2$—N]—

Step 2.1): —[N—$V^2$—N]—+—[$V^1$]—+—[N]—→Q$V^2$Q$V^1$,

Step 2.2): —[N—$V^1$—N]—+—[$V^2$]—+—[N]—→Q$V^1$Q$V^2$Q, where this variant, as mentioned above, can be carried out only with primary or secondary monoamines and where, with regard to the monomer units —[N]—, —[$V^1$]— and —[$V^2$]— used with preference, the above statements apply.

A further variant can be illustrated schematically, for example, as follows:

Step 1): —[N—N]—+—[$V^1$]—→—[N—N—($V^1$—N—N)$_x$]—

Step 2): —[N—N—($V^1$—N—N)$_x$]—+—[$V^2$]—→ where, with regard to the monomer units —[N—N]—, —[$V^1$]— and —[$V^2$]— used with preference, the above statements apply.

A further variant can be illustrated schematically, for example, as follows:

Step 1): —[N]—+—[$V^1$]—→—[N—($V^1$—N)$_x$]—

Step 2): —[N—($V^1$—N)$_x$]—+—[$V^2$]—→ where, with regard to the monomer units —[N]—, —[$V^1$]— and —[$V^2$]— used with preference, the above statements apply.

A further variant can be illustrated schematically, for example, as follows:

Step 1): x+1-[$V^1$]—+x—[N—N]—→—[$V^1$—(N—N—$V^1$)$_x$]—

Step 2): —[$V^1$—(N—N—$V^1$)$_x$]—+—[$V^2$]—→ where, with regard to the monomer units —[N—N]—, —[$V^1$]— and —[$V^2$]— used with preference, the above statements apply.

A further variant can be illustrated schematically, for example, as follows:

Step 1): x+1-[$V^1$]—+x—[N]—→—[$V^1$—(N—$V^1$)$_x$]—

Step 2): —[$V^1$—(N—$V^1$)$_x$]—+—[$V^2$]—→ where, with regard to the monomer units —[N]—, —[$V^1$]— and —[$V^2$]— used with preference, the above statements apply.

For all variants illustrated schematically above, it is also possible to use mixtures of monoamines —[N]— and diamines —[N—N]—.

The functional groups of the difunctional compounds capable of reaction with amino functions are more preferably selected from the group which consists of epoxy groups and haloalkyl groups.

The preferred starting point for the syntheses of the inventive linear polysiloxane copolymers are ($\alpha,\omega$ Si—H functionalized siloxanes of the general structure

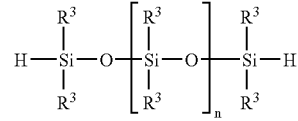

where $R^3$ is as defined above and n, depending on the desired repeat unit $V^1$ or $V^2$, is $n_2$ or $n_1$, each of which is as defined above. When they are not commercially available, these siloxanes can be prepared by known processes, for example by equilibration (Silicone, Chemie und Technologie [Silicones, Chemistry and Technology], Vulkan-Verlag, Essen 1989, p. 82-84).

The introductory insertion of the structural elements $V^{2*}$ and Q can be effected, for example, in two ways.

Firstly, it is possible first to bond unsaturated structures bearing tertiary anino functions, for example N,N-dimethylallylamine, by hydrosilylation directly to the siloxane in $\alpha,\omega$ arrangement. This process is common knowledge (B. Marciniec, Comprehensive Handbook on Hydrosilylation, Pergamon Press, Oxford 1992, p. 122-124).

Secondly, it is possible first to obtain reactive $\alpha,\omega$-functionalized intermediates by hydrosilylation, which can subsequently be converted to $\alpha,\omega$-ditertiary amino structures or directly to the inventive quaternary ammonium structures. Suitable starting materials for obtaining reactive intermediates are, for example, halogenated alkenes or alkynes, especially allyl chloride, allyl bromide, chloropropyne and chlorobutyne, unsaturated halocarboxylic esters, especially allyl chloroacetate, propargyl chloroacetate, allyl 3-chloropropionate and propargyl 3-chloropropionate and epoxy-functional alkenes, for example vinylcyclohexene oxide and allyl glycidyl ether.

The general performance of hydrosilylations with representatives of the substance groups mentioned is likewise known (B. Marciniec, Comprehensive Handbook on Hydrosilylation, Pergamon Press, Oxford 1992, p. 116-121, 127-130, 134-137, 151-155).

In a subsequent step, the reactive intermediates can then be reacted with compounds bearing secondary amino functions. Suitable representatives are N,N-dialkylamines, for example dimethylamine, diethylamine, dibutylamine, diethanolamine and N-methylglucamine, cyclic secondary amines, for example morpholine and piperidine, amino amides bearing secondary amino functions, for example the reaction products of diethylenetriamine or dipropylenetriamine with lactones such as γ-butyrolactone, δ-gluconolactone and glucopyranosylarabonolactone (DE-A 4318536, Examples 11a, 12a, 13a) or secondary-tertiary diamines, for example N-methylpiperazine. It is especially preferred to utilize appropriate imidazole or pyrazole derivatives, especially imidazole and pyrazole, to introduce tertiary amino functions.

Suitable partners for the epoxide derivatives used with preference in one embodiment are particularly the secondary-tertiary diamines mentioned, and also imidazole and pyrazole. In this way, the alkylations can be directed regioselectively and without additional complexity to the nitrogen atoms bearing hydrogen atoms.

To ensure a quantitative conversion of the reactive moieties to tertiary amino structures, the amines are used in a ratio of $1 \leq \Sigma$ secondary amino groups: reactive groups $\leq 10$, preferably from 1 to 3, especially from 1 to 2, very especially 1. Amine excesses have to be removed where appropriate.

The bonding of the above-described α,ω-ditertiary aminosiloxanes to monomer units —[$V^1$]— corresponding to $V^1$ or to a prepolymer unit —[$V^1$-(Q—$V^1$)$_x$]— leads to the formation of quaternary ammonium units and can in turn be effected in two advantageous ways.

Firstly, preference is given to separately obtaining a strongly hydrophilic, polyquaternary, difunctional precondensate —[$V_1$-(Q—$V^1$)]— which is combined at a suitable time with the α,ω-ditertiary aminosiloxanes and reacts to give the polyquaternary siloxane copolymer.

The preparation of highly charged, difunctional prepolymers of different chain length —[$V^1$-(Q—$V^1$)$_x$]— is described by way of example in WO 99/14300 (Examples 1 to 7, Table 11). Depending on the molar ratio of $V^1$ and the parent amine of Q, it is possible to obtain either a prepolymer terminated by amino groups according to the nature or a prepolymer terminated by other reactive groups.

In the case of bonding of a prepolymer terminated by amino groups —[N—($V^1$—N)$_x$]— to the amine function of an α,ω-ditertiary aminosiloxane structure, it is possible, for example, to use a quatermzing, difunctional monomer —[$V^1$]— corresponding to the repeat unit $V^1$, selected, for example, from bisepoxides, epichlorohydrin, bishaloalkyl compounds. It need not be mentioned that different $V^1$ groups may result in the prepolymer and in the connecting group between prepolymer and α,ω-ditertiary aminosiloxane structure.

In the case of a prepolymer terminated with reactive groups toward amino groups, such as —[$V^1$-(Q—$V^1$)$_x$]— there may a direct bond to the amine function of the α,ω-ditertiary aminosiloxane structure without further linker, i.e. connecting transitional or intermediate units, since an excess of the $V^1$-generating component has already been used in the prepolymer synthesis.

Alternatively to the separate preparation of a prepolymer —[$V^1$-(Q—$V^1$)$_x$]—, highly charged blocks can also be formed in parallel to the incorporation into the copolymer. This means that the α,ω-ditertiary aminosiloxane is initially charged together with the start components for the formation of —[$V^1$-(Q—$V^1$)$_x$]—, i.e., for example, —[$V^1$]— and mono- or diamines of the abovementioned definition —[N]— and/or —[N—N]—, and reacted.

Finally, it is possible to meter the α,ω-ditertiary aminosiloxane with long-chain siloxane unit $Z^2$ or short-chain siloxane unit $Z^1$, or the α,ω-difunctional siloxane [$V^{2*}$—$Z^2$—$V^{2*}$]— or —[$V^1$]— into the initially charged components for the formation of —[$V^1$-(Q—$V^1$)$_x$]— stepwise over a period of time, or else, conversely, to add these components stepwise to the α,ω-ditertiary aminosiloxane or α,ω-difunctional siloxane.

A preceding provision of prepolymers terminated by amino groups, for example —[N—($V^1$—N)$_x$]—, opens up the possibility of performing the copolymer formation directly with suitable reactive intermediates, for example epoxy derivatives. It is likewise preferred to initially charge the reactive intermediates and the start components together for the formation of —[$V^1$-(Q—$V^1$)$_x$]— and subsequently to react them.

Finally, it is possible to meter the reactive intermediates stepwise into the initially charged components for the formation of —[$V^1$-(Q—$V^1$)$_x$]— over a period of time, or else, conversely, to add these components stepwise to the reactive intermediates.

Irrespective of the selection of one of the above-described reaction paths and the closely associated question of whether amino units initially terminate the siloxane or else the prepolymer, the overall stoichiometry is selected such that the sum of the amino functions and the groups reactive with them is about 1:1.

In the context of the invention, it is possible to deviate from this preferred overall stoichiometry. However, products are then obtained which no longer have the maximum possible length, depending on the reactants, of the highly charged, hydrophilic —[$V^1$-(Q—$V^1$)$_x$]— block, but rather additionally leave behind an excess of an unreacted start component.

In addition to the above-described overall stoichiometry of the reaction, the selection of the component(s) forming the repeat unit $V^1$ is of great significance for the properties of the products.

Alkylene, alkenylene, alkynylene and aryl units are introduced preferably starting from the corresponding halides, especially chlorides and bromides. Exemplary representatives are 1,6-dichlorohexane, 1,4-dichlorobut(-2-)ene, 1,4-dichloro-but(-2-)yne and 1,4-bis(chloromethyl)benzene.

Polyalkylene oxide units may likewise be introduced via the α,ω-dihalogen compounds. These are obtainable from the oligomeric and polymeric alkylene oxides of the general composition

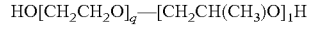

$$HO[CH_2CH_2O]_q—[CH_2CH(CH_3)O]_rH$$

where q and r are each as defined above, for example by chlorination of the hydroxyl groups with $SOCl_2$ (Organikum, Organisch-chemisches Grundpraktikum, 17th Edition, VEB Deutscher Verlag der Wissenschaften, Berlin 1988, p. 189-190).

Mono-, di- or polyhydroxy-functional units as the $V^1$ group may be introduced starting from epoxide derivatives.

Commercial examples are 1-chloro-2,3-epoxypropane, glycerol 1,3-bisglycidyl ether and diethylene glycol diglycidyl ether and neopentyl glycol diglycidyl ether.

When they are commercially unavailable, the desired diepoxides can be synthesized, for example, by reaction of the corresponding diols with 1-chloro-2,3-epoxypropane under alkaline conditions.

The scope of the invention includes the introduction of siloxane chains $Z^1$ into the structure of $V^1$. This gives rise to possibilities including that of using siloxane chains of different length for the formation of the overall molecule. It is a preferred variant to incorporate siloxane chains Z' of chain length range $n_2$=from 0 to 19, preferably from 0 to 15, more preferably from 0 to 10, especially from 0 to 5, more especially 0, into $V^1$. Suitable start materials for the incorporation are, for example, the corresponding α,ω-diepoxides.

In the reaction of epoxides with primary or secondary amines, it should be noted that one mole of $H^+$ per mole of epoxide/tertiary amine has to be added for alkylations of tertiary amino groups.

The selection of suitable amines as starting components for the formation of Q in the repeat unit —[$V^1$-(Q—$V^1$)$_x$]— likewise determines the molecular structure to a high degree. The use of ditertiary amines, for example N,N,N',N'-tetramethylethylenediamine, N,N,N',N'-tetramethyltetramethylenediamine, N,N,N',N'-tetramethylhexamethylenediamine, N,N'-dimethylpiperazine, leads to products in which each nitrogen atom of the repeat unit has been quaternized.

The use of secondary-tertiary diamines, for example N-methylpiperazine, opens up the path to repeat units —[$V^1$-(Q—$V^1$)$_x$]— in which tertiary and quaternary amine and ammonium structures are present in a ratio of 1:1. A partial or full subsequent quaternization of remaining tertiary amino structures constitutes a preferred variant for the establishment of a desired high density of the quaternary ammonium groups. The corresponding aromatic amines imidazole or pyrazole lead to products with a delocalized charge.

When primary-tertiary diamines, for example N,N-dimethylpropylene-diamine and 1-(3-aminopropyl)imidazole, are used, especially in combination with diepoxides, comb-like structures can be formed, for which the degree of quaternization during a subsequent alkylation can be selected. In principle, degrees of quaternization of an average of less than one quaternary ammonium group per repeat unit —[$V^1$-(Q—$V^1$)$_x$]— can be established. However, it is preferred to quaternize at least one nitrogen atom per repeat unit.

Starting from disecondary amines, for example piperazine, N,N'-bis(2-hydroxyethyl)hexamethylenediamine, N,N'-bis(2-hydroxypropyl)hexamethylenediamine, it is also possible in principle to synthesize repeat units —[$V^1$-(Q—$V^1$)$_x$]— with an average number of less than one quaternary ammonium group. In this case, the disecondary amines initially afford polytertiary, amino-modified siloxane copolymers or else prepolymers which can be quaternized in a final reaction partly or fully to —[$V^1$-(Q—$V^1$)$_x$]—. However, it is preferred in this variant too to quaternize at least one nitrogen atom per repeat unit.

Suitable quaternizing agents include the commonly known substance groups such as alkyl halides, halocarboxylic esters, epoxide derivatives in the presence of $H^+$, and dialkyl sulfates, especially dimethyl sulfate.

Commercially unavailable disecondary amines are prepared in a preferred embodiment starting from the corresponding diprimary amines, for example hexamethylenediamine, by alkylation with epoxides, for example ethylene oxide, propylene oxide, isopropyl glycidyl ether, with utilization of the different reaction rates of primary and secondary amines.

It has already been explained that the possibility exists within the scope of the invention of introducing siloxane chains $Z^1$ into the structure of $V^1$. Suitable start materials mentioned by way of example have been the reactive intermediates α,ω-diepoxides.

Preferred anions $A^-$ which neutralize the positive charges resulting from the ammonium groups are the ions formed during the quaternization, such as halide ions, especially chloride and bromide, alkysulfates, especially methosulfate, carboxylates, especially acetate, propionate, octanoate, decanoate, dodecanoate, tetradecanoate, hexadecanoate, octadecanoate, oleate, sulfonates, especially toluenesulfonate. However, it is also possible to introduce other anions by ion exchange. Examples include organic anions such as polyether carboxylates and polyether sulfates.

The introduction of the functional group of the formula (I), which is illustrated in detail below, comprises, for example:
a) the reaction of diisocyanates comprising the functional group of the formula (I) with at least one mole of a diamine (1) to form a monomeric, oligomeric or polymeric diamine (2) which comprises the functional group of the formula (I) or
b) the reaction of one mole of a diisocyanate containing the functional group of the formula (I) with at least one mole of a multifunctional, preferably difunctional, organic compound (1) capable of reaction with the isocyanate groups and amino groups to form a multifunctional, preferably difunctional, monomeric, oligomeric or polymeric organic compound (2) which is capable of reaction with amino groups and contains the group of the formula (I), or
c) the reaction of one mole of a diisocyanate containing the functional group of the formula (I) with at least one mole of a multifunctional, preferably difunctional, organic compound (1) capable of reaction with the isocyanate groups to form a multifunctional, preferably difunctional, organic monomeric, oligomeric or polymeric compound (2) containing the functional group of the formula (I) and terminal groups capable of reaction with isocyanate groups, conversion of the organic compound (2) mentioned to a multifunctional, preferably difunctional, monomeric, oligomeric or polymeric organic compound (3) capable of reaction with amino groups and the use of the resulting compounds containing the group of the formula (I) in the processes a) to d) of the above-described process.

The introduction of the functional group of the formula (II), which is illustrated in detail below, comprises, for example, the reaction of an amine compound selected from a diamine compound and/or a primary, secondary or tertiary monoamine compound containing the unit of the formula (II), and/or the reaction of a multifunctional, preferably difunctional, organic compound containing the unit of the formula (II).

In the process for preparing the inventive compounds, the functional groups of the multifunctional, preferably difunctional, compounds capable of reaction with amino functions are preferably selected from the group which consists of epoxy groups and haloalkyl groups.

The inventive compounds which contain a functional group of the formula (I)

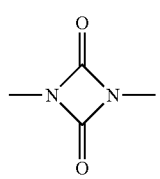

(I)

have the group of the formula (I) mentioned appropriately in a V group.

The inventive compounds which have the functional group of the formula (I) preferably contain the unit of the formula (Ia)

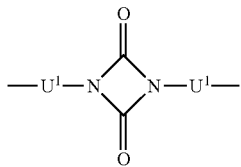
(Ia)

in which
U¹ is selected from the group which consists of divalent radicals of the formulae:

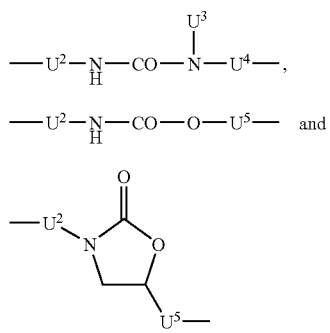
(Ib)
(Ic)
(Id)

where
U² is bonded to the nitrogen atom of the functional group of the formula (I), and U² is a divalent, straight-chain, cyclic or branched, saturated, unsaturated or aromatic hydrocarbon radical which has up to 100, preferably up to 30, carbon atoms and may contain one or more —O— groups, U² is preferably a divalent, straight-chain hydrocarbon radical having up to 15 carbon atoms, for example hexamethylene, divalent, cyclic hydrocarbon radicals having up to 15 carbon atoms, for example based on biscyclohexylmethane structures

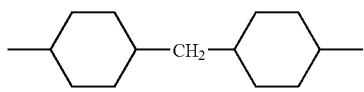

divalent, branched hydrocarbon radicals having up to 15 carbon atoms, for example based on methylcyclohexyl or isophorone structures

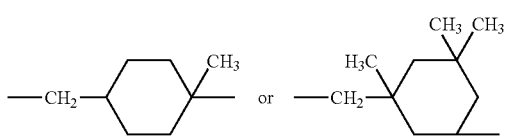

divalent, aromatic hydrocarbon radicals having up to 15 carbon atoms, for example based on 2,4-tolyl, 2,6-tolyl, bisphenylmethane and naphthylene structures.

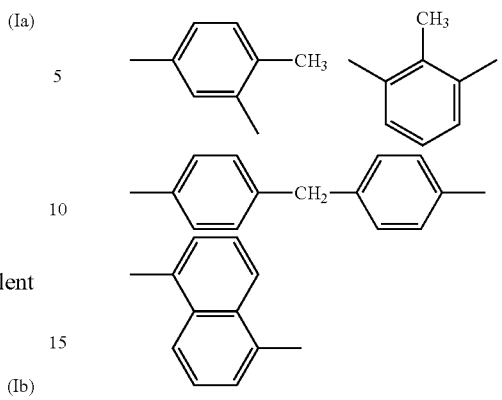

U³ may be hydrogen or a monovalent, straight-chain, cyclic or branched, saturated, unsaturated or aromatic hydrocarbon radical which has up to 100, preferably to 30, carbon atoms and may contain one or more —O— groups and be substituted by OH.

U⁴ and U⁵ are each divalent straight-chain, cyclic or branched, saturated, unsaturated or aromatic hydrocarbon radicals which have up to 1000, preferably up to 200, more preferably up to 100, carbon atoms and may optionally contain one or more groups selected from —O—, —C(O)—,

—NR²— in which R² is as defined above, and which may optionally be substituted by one or more hydroxyl groups, with the proviso that the

and —NR²— groups are bonded to a carbonyl carbon atom.

U³ may additionally consist of the —W—Si(OR)$_{3-a}$(R')$_a$ groups in which R, R' and a are each as defined above and W is a divalent, straight-chain, cyclic or branched, saturated, unsaturated or aromatic hydrocarbon radical which has up to 100 carbon atoms and may contain one or more —C(O)—, —O—, —NH—, —S— groups, and may optionally be substituted by hydroxyl groups.

U³ is preferably a monovalent, straight-chain, cyclic or branched, saturated, unsaturated hydrocarbon radical which has up to 15 carbon atoms and may contain one or more —O— moieties and silicon atoms and be substituted by OH, for example methyl, ethyl, propyl, butyl, hexyl, and also radicals of the following formulae

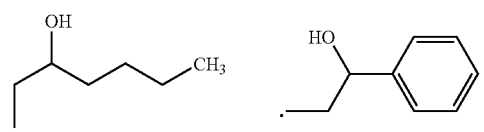

-continued

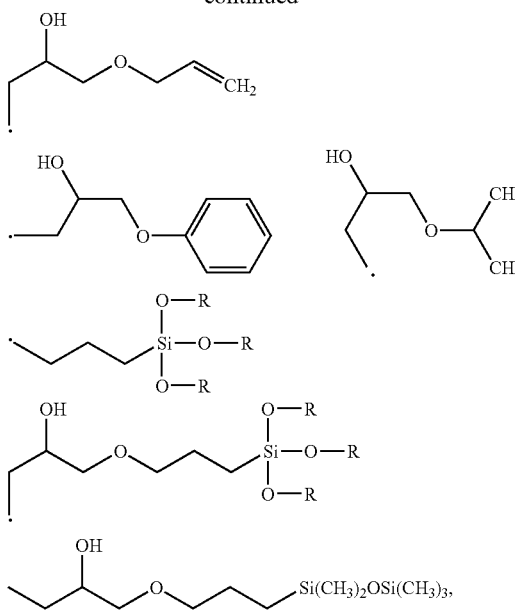

where the $U^3$ radicals which contain trialkoxysilyl groups lead to compounds which have both functional groups of the formula (I) and functional groups of the formula (II).

$U^4$ and $U^5$ groups such as alkylene units, for example dimethylene, trimethylene, hexamethylene or alkylene ester units, especially derived from esterified alkanediols, alkenediols, alkynediols and polyalkylene oxides, for example

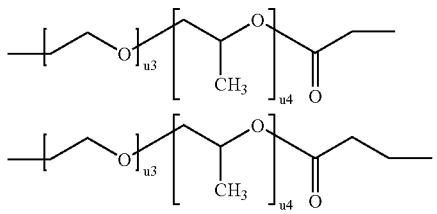

or oligoalkylene oxide units, for example

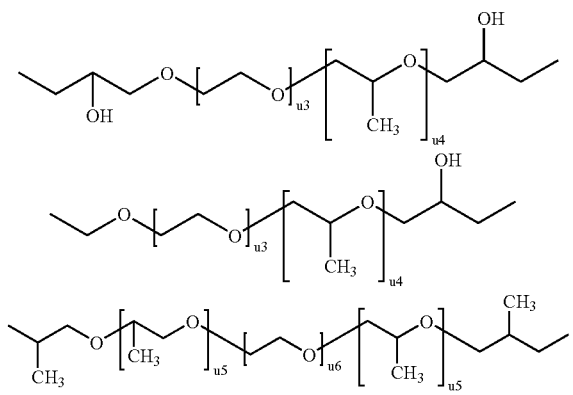

or polysiloxane-containing units, for example

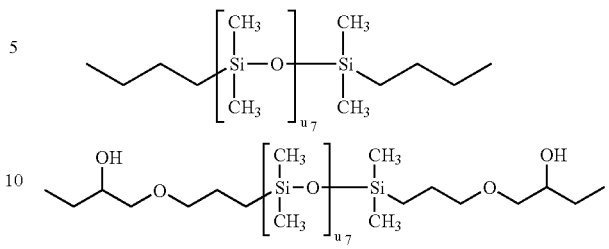

where $u_3$ is from 0 to 100, $u_4$ is from 0 to 100, $u_3 + u_4 \geq 1$, $u_5$ is from 1 to 100, $u_6$ is from 1 to 100, $u_7$ is from 1 to 300.

To introduce the units of the formula I into the inventive polyquaternary polysiloxane copolymers, monomers having uretdione substructures, preferably of the

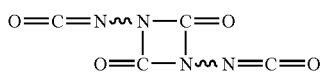

type are initially appropriately prefunctionalized.

The wavy line indicates that the spacers are in principle freely selectable, i.e. at least divalent linking $U^2$ groups between the uretdione structure and the isocyanate groups. This includes the case that further reactive isocyanate groups are present in the start molecules.

These start molecules are obtained by dimerization of appropriate isocyanates, preferably diisocyanates (H. J. Laas, R. Halpaap, J. Pedain, Journal f. Prakt. Chemie 336 [1994], 185-200; H. J. Laas, R. Halpaap, J. Pedain, Farbe+Lack 100 [1994], 330-336) and are commercially available from Bayer A G Leverkusen under the name DESMODUR®. Particularly preferred diisocyanates are hexamethylene diisocyanate, isophorone diisocyanate, bis(4-isocyanato-cyclohexyl)methane, toluylene 2,4-diisocyanate, tolylene 2,6-diisocyanate, bis(4-isocyanatophenyl)methane, naphthylene 1,5-diisocyanate, 1-isocyanato-1-methyl-4(3)-isocyanatomethylcyclohexane, 5-methyl-1,9-diisocyanatononane, 2,4-dimethyl-1,8-diisocynatooctane, 2-methyl-1,5-diisocyanatopentane and 2-ethyl-1,4-diisocyanatobutane.

According to formulae I(b) to I(d), the uretdione structures are linked to the rest of the molecule via urea, urethane and oxazolidinone groups which bond to or merge into a $U^4$ or $U^5$ group.

$U^4$ or $U^5$ is formed by reaction of precursors of $U^4$ or $U^5$, such as difunctional compounds of the aminoalkyl, hydroxyalkyl and epoxyalkyl type, with isocyanate. By definition, it is possible that only part of the molecule of the precursors reacting with isocyanate groups is reproduced by the $U^4$ or $U^5$ or V unit, and the remaining part, when it is, for example, an amino group which has not been reacted with isocyanate, i.e. has not been to a ureido group converting unit, falls under the definition of Q.

The difunctional amino compounds which react with the preferred uretdione-containing diisocyanates are, for example, diprimary diaminoalkyl compounds such as ethylenediamine, 1,2-propylenediamine, 1,3-propylenediamine and 1,6-hexanediamine, siloxane-containing diprimary diaminoalkyl compounds such as α,ω-aminopropyl-substituted straight-chain siloxanes, diprimary diamino polyethers of the ethylene oxide and/or propylene oxide type, such as the Jeffamine® of the ED series (Huntsman Corp.), primary-secondary diaminoalkyl compounds, for example 2-hydroxyethyl-ethylenediamine, N-(2-aminoethyl)piperazine, silicon-containing primary-secondary diaminoalkyl compounds, for example aminoethylaminopropyl-substituted alkoxysilanes of the Dynasilan® series (Degussa), disecondary diaminoalkyl compounds, for example piperazine, siloxane-containing disecondary diaminoalkyl compounds, such as the reaction products of α,ω-diglycidyl-substituted straight-chain siloxanes with monofunctional primary amines, silyl-containing disecondary diaminoalkyl compounds, for example the reaction products of α,ω-glycidyl-substituted polyethers (DER® types Dow Chemicals) with aminopropyl-substituted or aminoethylaminopropyl-substituted alkoxysilanes (Dynasilano series Degussa) or the reaction products of diprimary amines with epoxy-functionalized alkoxy silanes (GLYMO Silan® Degussa), disecondary diamino polyethers of the ethylene oxide and/or propylene oxide type, such as the reaction products of α,ω-glycidyl-substituted polyethers (DER® types Dow Chemicals) with monofunctional primary amines or the reaction products of diprimary diamino polyethers of the ethylene oxide and/or propylene oxide type, such as the Jeffamine® of the ED series (Huntsman Corp.), with monofunctional epoxides, primary-tertiary diaminoalkyl compounds such as N,N-dimethylpropylene-diamine and N-(3-aminopropyl)imidazole, secondary-tertiary diaminoalkyl compounds such as N-methylpiperazine.

The difunctional hydroxy compounds which react with the preferred uretdione-containing diisocyanates are, for example, hydroxy-functionalized tertiary amines which are obtained by mono-/oligoalkoxylation of corresponding molecules having secondary amino functions, such as 2-hydroxyethyldimethylamine, N-(2-hydroxyethyl)-N'-methylpiperazine and hydroxy-functionalized esters of halocarboxylic acids, especially monoesters of monohalocarboxylic acids with diols, quite especially of chloroacetic acid and 3-chloropropionic acid, for example $HOCH_2CH_2OC(O)CH_2Cl$, hydroxy-functionalized epoxides such as glycidol.

The difunctional epoxy compounds which react with the preferred uretdione-containing diisocyanates are, for example, diepoxides based on alkylene oxides, especially of the ethylene oxide and/or propylene oxide type, such as α,ω-glycidyl-substituted polyethers of the DER® type (Dow Chemicals)

α,ω-glycidyl- or α,ω-cyclohexyloxy-substituted straight-chain polydiorganosiloxanes.

The $U^4$ and $U^5$ groups are bonded via functional structures, preferably based on esters, hydroxyalkyl units with amine or quaternary ammonium units Q, and are attached to the rest of the molecule via Q and also further V units. This means that the $U^4$ and $U^5$ groups can firstly have alkylating action during the attachment reaction, as in the case of the ester and hydroxyalkyl units. The $U^2$, $U^3$, $U^4$ and $U^5$ groups thus fall under the definition of V; they are substructures of V.

In one embodiment, the inventive compound of the formula (IV) has, in at least one of the V and/or Q groups, a group of the formula (II)

in which a, R and R' are each as defined above.

A further embodiment of the inventive compounds is characterized in that it has at least one unit Q which contains an $R^1$ radical which has a group of the formula (II).

A further embodiment of the inventive compounds is characterized in that it has at least one unit V which contains a group of the formula (II).

In a further embodiment of the inventive compounds, they contain a unit Q having at least one $R^1$ radical of the formula (VIIIa)

in which $U^6$ is a divalent straight-chain, cyclic or branched, saturated, unsaturated or aromatic hydrocarbon radical which has up to 100 carbon atoms and may optionally contain one or more groups selected from —O—, —C(O)—, —NH— and —$NU^8$—, or may optionally be substituted by one or more hydroxyl groups, in which $U^8$ is hydrogen or a monovalent, straight-chain, cyclic or branched, saturated, unsaturated or aromatic hydrocarbon radical which has up to 100 carbon atoms and may contain one or more —O— groups and be substituted by OH, with the proviso that —NH— and —$NU^8$— is bonded to a carbonyl and/or thiocarbonyl carbon atom, and $U^7$ is a monovalent, straight-chain, cyclic or branched, saturated, unsaturated or aromatic hydrocarbon radical which has up to 20 carbon atoms and may contain one or more —O— groups and be substituted by OH, with the proviso that the $U^7$ radicals may be the same or different and at least one $U^7$ radical per silicon atom is bonded to the silicon atom via —O—.

The functional groups of the formula (VIII) may occur as an $R^1$ radical in the Q units, as $U^3$, $R^2$ or radicals bonded via CH, amide, ester, ether, or as $R^3$ radicals in the V units.

The groups which have the formula (VIII) may be introduced using silanes containing primary, secondary, tertiary amino groups of the formula (IX), for example

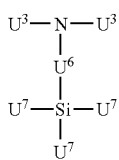
(IXa)

in which $U^3$, $U^6$ and $U^7$ are each as defined above. Depending on the degree of alkylation or time of the addition, they can act as polymer chain terminators in the co- or terpolymerization, especially when they are tertiary amines.

When silanes containing primary amino groups and/or a plurality of amino groups are used, the stoichiometry of the overall reaction should be taken into account for this purpose. Examples of preferred materials are

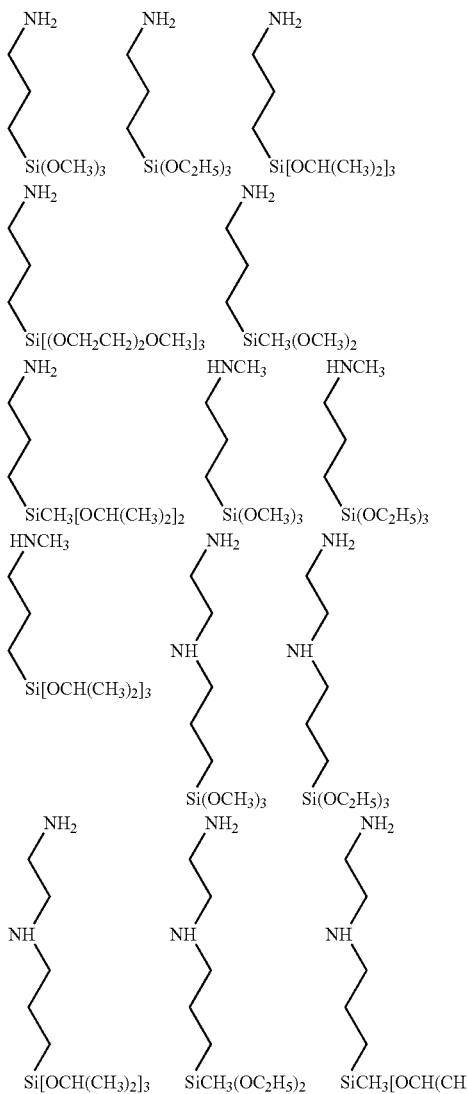

The structure of the amino group decides the type of bonding to the polymer molecule, while the substitution pattern on the silicon atom can control the rate of hydrolysis in aqueous environment and the final network density. Generally, bulky alkoxy substituents lead to slowing of the hydrolysis in aqueous environment. The partial introduction of unhydrolyzable alkyl substituents reduces the functionality of the network density and thus the extent of crosslinking.

Aminosilanes of the types shown at either commercially available (Dynasilane® Degussa) or can be converted to the desired materials, for example, by base-catalyzed exchange of alkoxy groups on the silicon atom.

It is also possible to obtain specific start silanes by alkylating ammonia or primary amines with, for example, epoxy-functionalized silanes such as

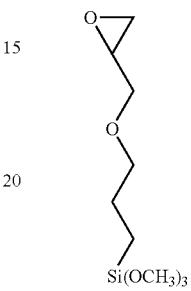

or the analogous cyclohexyloxy derivative.

Preferred starting materials are also monofunctional silanes containing primary amino groups (IXb):

(IXb)

They act as polymer chain extenders when the polymer formation reaction is effected as a double alkylation of the nitrogen atom for chain propagation. The degree of alkylation or a suitable adjustment of the overall stoichiometry of the polymer formation reaction enables this. Examples are:

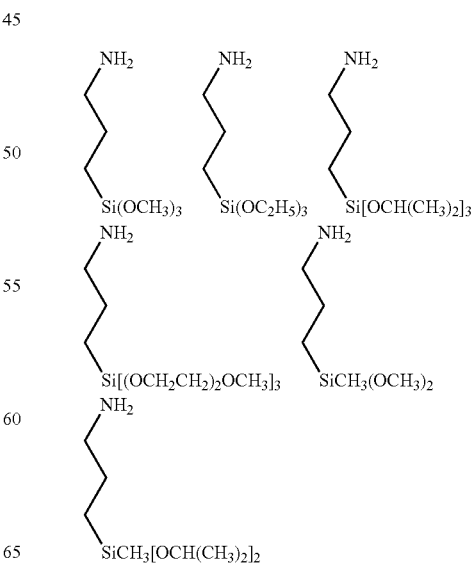

Preferred starting materials are also silanes containing tertiary amino groups (IXa):

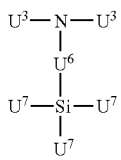

(IXa)

They act as polymer chain terminators when the tertiary amino group can be quaternized in the course of the polymer formation reaction. Suitable start silanes, particularly methylated derivatives, may be obtained by hydrosilylation of, for example, N,N-dimethylallylamine with appropriate H-silanes. Alternatively, it is possible to react epoxy-functionalized silanes such as

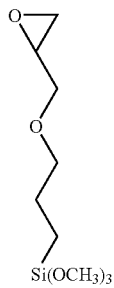

or the analogous cyclohexyloxy derivative as a reaction product with secondary amines such as dimethylamine or more complex methylated amines such as N-methylpiperazine.

The reaction of isocyanatosilanes such as 3-isocyanatopropyltriethoxysilane (ABCR GmbH), with primary-tertiary diamines, for example N,N-dimethylpropylenediamine and N-(3-aminopropyl)imidazole, secondary-tertiary diamines, for example N-methylpiperazine, hydroxy-functional amines, for example 2-hydroxyethyldimethylamine and more complex amines such as N-(2-hydroxyethyl)-N'-methylpiperazine, likewise leads to the desired start silanes.

It is likewise possible to convert silanes having primary or secondary amino functions, such as

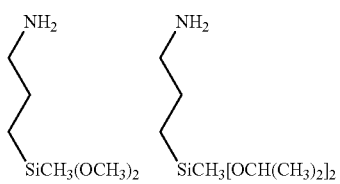

to the desired tertiary structures using monofunctional epoxides. Finally, it is possible, on completion of the polymer formation reaction of the formula (IX), to convert any quaternizable amino groups to quaternized ammonium groups by alkylation with suitable alkylating agents.

Further starting materials are silanes containing tris-tertiary amino groups:

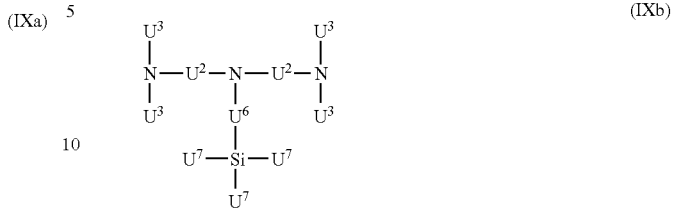

(IXb)

in which $U^2$, $U^3$, $U^6$ and $U^7$ are each as defined above. The compounds (IX), like all divalent or higher-valency amines, can act as polymer chain extenders when they are reacted with a divalent or higher-valency alkylating agent, i.e. when two tertiary amino groups can be quaternized in the course of the polymer formation reaction. Suitable start silanes, particularly N-methylated derivatives, can preferably be obtained by alkylation of triamines which have two tertiary and one secondary amino function with epoxy-functionalized silanes such as

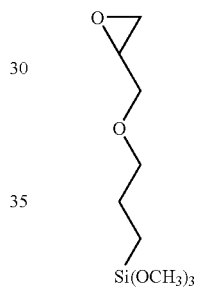

or the analogous cyclohexyloxy derivative. An example of a preferred triamine is N,N,N',N'-tetramethyldipropylenetriamine (Jeffcat®ZR50B, Huntsman Corp.). The use of N-methylated amino components, especially of N,N-dimethyl structures ensures that the subsequent incorporation of these monomers into the polymer molecule proceeds virtually regioselectively on the methylated nitrogen atoms.

It is likewise possible to react triamines such as N,N,N',N'-tetramethyldipropylenetriamine with monofunctional isocyanatosilanes, for example 3-isocyanatopropyltriethoxysilane (ABCR GmbH). In this case, the start silane which is then formed has two tertiary amino groups and one urea moiety.

Such isocyanatosilanes likewise open up the possibility of utilizing ditertiary amines with additional hydroxyl function as the amine basis. Examples are corresponding ethylene oxide and propylene oxide derivatives such as N,N-bis(3-dimethylaminopropyl)-N-isopropanolamine (Jeffcat®ZR50, Huntsman Corp.) and N,N,N'-trimethyl-N'-hydroxyethyl-bisaminoethyl ether (Jeffcat®ZF10, Huntsman Corp.). As a result of such a prefunctionalization, ditertiary amines are obtainable which bond to the silane moiety via a urethane structure.

For the formation of primarily oligomerized silane structures, preference is given to α,ω-NH terminated oligostructures as the starting material.

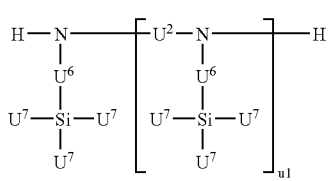

(IXc)

in which $U^2$, $U^6$, $U^7$ are each as defined above, and $u_1$ is from 0 to 10.

For their synthesis, the preferred start materials are monofunctional primary aminosilanes such as 3-aminopropylsilanes, and diepoxy derivatives, for example diepoxides based on alkylene oxides, especially of the ethylene oxide and/or propylene oxide type, such as α,ω-glycidyl-substituted polyethers of the DER® type (Dow Chemicals) and α,ω-glycidyl- or α,ω-cyclohexyloxy-substituted straight-chain siloxanes. Controlled adjustment of the stoichiometry between difunctional aminosilane component and diepoxide allows a prepolymer (LXc) which is α,ω-NH-terminated to be obtained in an oligomerization reaction and incorporated into the subsequent polymerization process. To achieve this α,ω-NH termination, an excess of aminosilane component is needed.

To form principally oligomerized silane structures (IXd), the concept explained above for obtaining the oligo structures is modified to the effect that secondary-tertiary diaminosilanes are fed into the oligomerization process in a defined amount, preferably offset in time.

These are silanes which are preferably obtained by reaction of primary-tertiary diamines, such as N,N-dimethylpropylenediamine and N-(3-aminopropyl)imidazole, with epoxy silanes, for example of glycidyl and cyclohexyloxy type. These secondary-tertiary diaminosilanes are added to the binary system consisting of mono-(primary amino)-functional silane and diepoxy derivative and lead, determined by reactivity and sequence since they are monofunctional, to a prepolymer which is terminated in the α,ω arrangement by tertiary amino groups, preferably N,N-dimethyl groups, and is shown in the following formula:

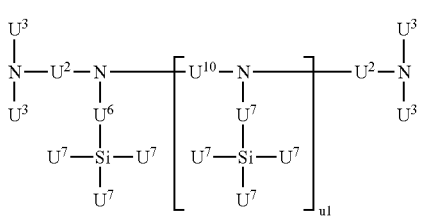

(IXd)

in which $U^3$, $U^6$ and $U^7$ and $u_1$ are each as defined above and $U^{10}$ is a divalent organic radical.

These terminal tertiary amino groups may finally be utilized for chain extension in the polymerization process.

To extend illustrated the principally oligomerized silane structures (Xa), preference is given to α,ω-epoxy-terminated oligo structures as the starting material

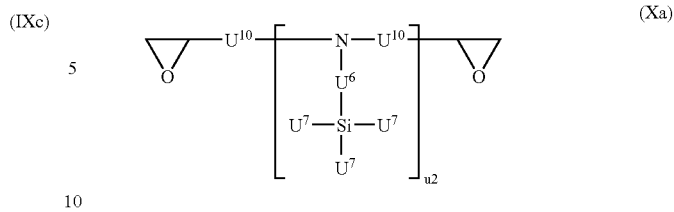

(Xa)

in which $U^3$, $U^6$, $U^7$, $U^{10}$ are each as defined above and $u_2$=from 1 to 10.

To synthesize (Xa), the concept outlined above is modified in such a way that controlled adjustment of the stoichiometry between difunctional aminosilane component and diepoxide during the oligomerization reaction produces a condensate which is α,ω-epoxy-terminated and can be incorporated into the subsequent polymerization process. To achieve this α,ω-epoxy termination, an excess of diepoxide is needed.

Preferred starting materials are in turn monofunctional primary aminosilanes such as 3-aminopropylsilanes, and diepoxy derivatives, for example diepoxides based on alkylene oxides, especially of the ethylene oxide and/or propylene oxide type, such as α,ω-glycidyl-substituted polyethers of the DER® type (Dow Chemicals) and α,ω-glycidyl- or α,ω-cyclohexyloxy-substituted straight-chain siloxanes.

The provision of such silylalkoxy-containing prepolymers does not only lead to a great increase in the amine and ammonium units in this segment, but also to a high concentration of crosslinkable alkoxysilyl units. This allows substantivity and hydrophilicity to be imparted by these polymer blocks to a particular degree.

The monomers needed to incorporate the inventive uretdione substructures of the formula (I) and silane substructures of the formula (II) preferably have alkylatable groups of the types primary amine
secondary amine
tertiary amine and alkylating groups of the types halocarboxylic ester
epoxide.

To successfully introduce these monomers into the polymer molecules, their molar content of alkylatable groups or alkylating groups has to be included in the molar overall assessment of the polymer formation reaction. Details of these assessments are laid out, for example, in WO 02/10256, WO 02/10257, WO 02/10259 and DE 100 36 533, DE 100 36 522, EP 282720, U.S. Pat. No. 6,240,929, DE 33 40 708, DE 102 12 470.1, DE 102 51 525.5 and DE 102 51 526.3.

For the inventive overall reactions, it is preferably the case that, essentially, Σmole (primary+secondary+tertiary) amine=Σmole of alkylating groups.

Depending on the type of the intended polymer formation reaction, a primary amino group can be included in the calculation as mono-, di- or trivalent. Secondary amines may occur in mono- or divalent form.

Deviations from this molar overall assessment are possible. Advantageously, deviations from a balanced molar overall assessment can be utilized to obtain materials with specific end groups. For example, amino end groups can be obtained by controlled molar excess of amino monomers. The inventive uretdione substructures of the formula (I) and silane substructures of the formula (II) are involved in the overall polymer structure to an extent of from 0.01 to 50 mol %, preferably from 0.01 to 30 mol %, very preferably from 1 to 30 mol %, especially from 1 to 10 mol % and from 10 to 30 mol %.

The incorporation of the inventive reactive substructures of the formulae (I) and/or (II) enables controlled activation of the polymer molecules in the application. For instance, it is possible to activate the uretdione structures thermally and/or catalytically and in the presence of functional groups on substrate surfaces. In addition, the density of the uretdione structures in the polymer molecule and their chemical nature, i.e., for example, their origin from aliphatic or aromatic diisocyanates, are parameters which can be utilized to control the activation. The inventive alkoxy silyl or alkoxy silane structures can be activated, for example, by the addition of water, pH changes, temperature increases and functional groups on the substrate surfaces. It is possible via the density of the silyl moieties and particularly the chemical constitution of the alkoxy groups to control the degree of crosslinking and the rate of activation, for example by selective hydrolysis.

It is thus a considerable advantage of the polymer molecules modified by the functional, reactive substructures of the formulae (I) and (II) that they can be preformulated and stored appropriately before the expected application. Only after activation in the actual application does the very high substantivity of the polymers modified in accordance with the invention become fully active by virtue of molecular weight increase, crosslinking, fixing or enclosing the substrate, or reaction with functional groups on the substrate surface.

The polymer formation reactions are performed preferably in water, polar organic solvents or mixtures of the two components mentioned. Suitable examples are alcohols, especially methanol, ethanol, i-propanol and n-butanol, glycols such as ethylene glycol, diethylene glycol, triethylene glycol, the methyl, ethyl and butyl ethers of the glycols mentioned, 1,2-propylene glycol and 1,3-propylene glycol, ketones such as acetone and methyl ethyl ketone, esters such as ethyl acetate, butyl acetate and 2-ethylhexyl acetate, ethers such as tetrahydrofuran, and nitro compounds such as nitromethane. The selection of the solvent depends substantially upon the solubility of the reactants, the desired reaction temperature and any reactivity present which disrupts the reaction.

The reactions are performed in the range from 20° C. to 130° C., preferably from 40° C. to 100° C.

A limitation of the molecular weight is brought about, for example, by the termination which arises as a result of any water or alcohol present in the reaction between epoxides and in the reaction system, or alternatively by the additional use of tertiary amines such as trialkylamines, or the addition of monofunctional compounds reactive toward amino groups. This means that the polyorganosiloxane polymers, in addition to the terminal groups which result from the reaction of the monomeric starting materials by its nature, also have those from monofunctional chain terminators such as trialkylamines, etc., and, for example, ammonium, amino, ether or hydroxyl end groups resulting therefrom.

The inventive amino- and/or ammoniopolysiloxane compounds also allow the preparation of formulations which comprise at least one of these compounds.

It is also possible to prepare formulations which comprise at least one solvent. These solvents are selected from water and organic solvents such as $C_1$-$C_{22}$ aliphatics or $C_6$-$C_8$ aromatics, preferably $C_1$-$C_{22}$-alcohols, esters and/or ethers.

The formulations are in particular in the form of an aqueous emulsion, preferably in the form of an aqueous microemulsion. Microemulsions are emulsions in which the dispersed phase has particles with a mean size of from 10 to 250 nm. In these emulsions, the inventive polymers themselves may serve as emulsifiers.

Laundry detergent formulation comprising at least one of the inventive compounds, especially those having nonionogenic and/or anionic surfactants and cosmetic formulations.

The inventive compounds or formulations may in turn themselves be utilized for the preparation of further subsequent formulations for finishing or treating of natural or synthetic fibers or fiberlike substrates and for cosmetic application, which are suitable for the treatment or application of natural or synthetic fibers or fiberlike substrates including paper and in cosmetic applications.

The invention thus also includes processes for treating and/or finishing natural or synthetic fibers or fiberlike substrates which utilize the wetting treatment of natural or synthetic fibers or fiberlike substrates, and, if appropriate, the activation with at least one of the inventive compounds. The term paper includes webs, pulps, layers or coatings which subsequently find use in wiping cloths or tissues and cleaning cloths in order to improve the use properties such as hand, hydrophilicity or strength and stiffness.

These processes include the contacting, such as immersion, rinsing, spraying and transfer application (printing or pressing), extruding or calendaring.

The invention thus additionally also encompasses natural or synthetic fibers or fiberlike substrates including paper which have been treated with at least with one of the inventive compounds and products produced therefrom, such as textiles, papers, webs and also coated moldings with metallic, varnish or plastics surfaces. The surfaces become more hydrophilic, more wettable or antistatic and in spite of this have a velvetlike soft, silicone-like hand.

The quaternized polysiloxane copolymers modified by the substructures (I) and (II) in accordance with the invention can therefore also be used advantageously in cosmetic formulations for skincare and haircare, such as "rinse-off" products, for example 2-in-1 shampoos, body wash and hair rinses for aftertreatment of hair after washing or dying, or the pretreatment of hair before bleaching, curling or straightening, and also so-called "leave-in" products such as hair treatments, care creams, styling creams, hair gels, hairstyling products, hairsetting compositions, hairsprays, pump sprays, hairdrier waving compositions and hairdrier hairsetting compositions. The inventive materials bring about an improvement in the wet combing forces and dry combing forces, an improvement in the hair volume and the shine, and also a reduction in the washout of dyes from or out of tinted or dyed hair. For cosmetic applications, preference is given to using polymers with the structural units of the formula (II).

The quaternized polysiloxane copolymers modified by the reactive substructures of the formula (I) and (II) in accordance with the invention may also be used advantageously in finishes for the treatment and finishing of hard surfaces, in formulations for drying automobiles and other hard surfaces after machine washing, for finishing textiles and textile fibers, as a separate softener after the washing of textiles with anionic/nonionogenic detergent formulations, as a softener in formulations based on anionic/nonionogenic surfactants for textile laundry, as an ironing aid, means for preventing or reversing textile creases and means for paper treatment before and after dewatering. The inventive quaternary copolymers allow the wetting behavior toward water and soil, the electrostatic properties and the cleaning performance to be influenced within wide limits. In the case of fibers, they increase, for example, important cosmetic properties such as shine, fullness and combability or softness, stiffness and strength, by being fixable to the substrate over a long period.

EXAMPLES

The examples which follow are intended to illustrate the invention in detail but without restricting it.

Example 1

1a) In a 500 ml three-neck flask, 0.705 g (6.9 mmol) of N,N-dimethyl-1,3-propanediamine is dissolved at room temperature in 50 ml of isopropanol. Subsequently, 1.81 g (16% NCO content; 6.9 mmol of —NCO) of the isophorone diisocyanate dimer of the structure

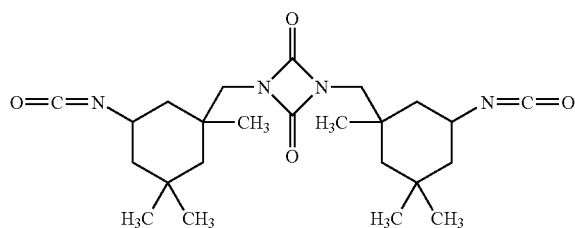

were added dropwise within a few minutes at such a rate that a clear solution is always retained. On completion of the dropwise addition, the solution is heated to 60° C. for 1 hour. A ditertiary amine of the structure

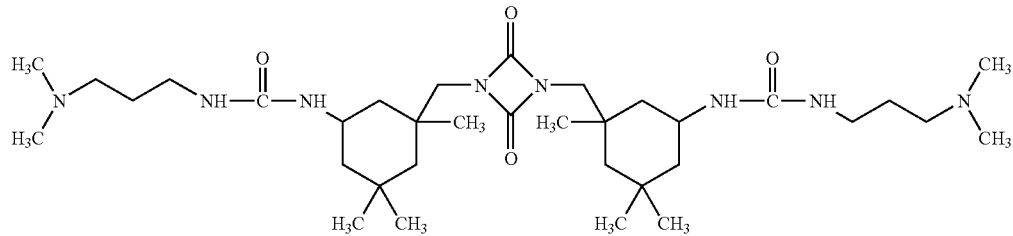

is formed.

1b) 4 g of deionized water, 1.04 g (17.27 mmol) of acetic acid, 3.45 g (17.27 mmol) of dodecanoic acid, 1.78 g (20.72 mmol of tertiary amino groups) of N,N,N',N'-tetramethyl-1, 6-hexanediamine and 2.19 g (6.9 mmol of primary amino groups) of an alkylene oxide derivative which is obtainable under the trade name Jeffamin® ED 600 and has the structure

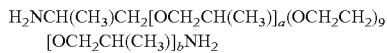

where a+b=3.6 are dissolved in 50 g of isopropanol.

1c) 100 g (34.54 mmol of epoxide groups) of a diepoxide of the structure

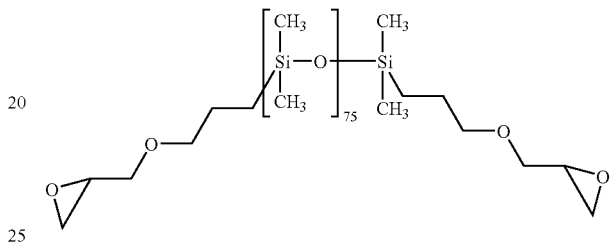

are initially charged in a three-neck flask. Subsequently, solutions 1a) and 1b) are added dropwise in their entirety with stirring. On completion of addition, the overall mixture is heated to 80-82° C. for 10 hours. 204.6 g of a yellowish, opaque solution are obtained (solids content 52.5%), which contains a polymer which, inter alia, contains the with the structural units

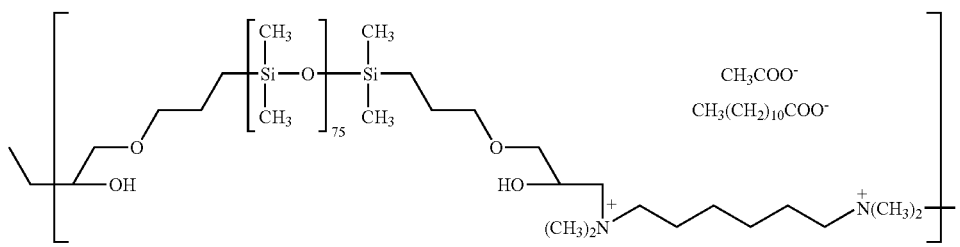

-continued

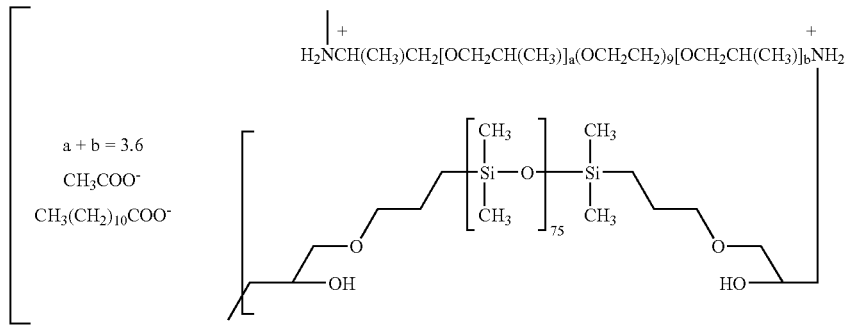

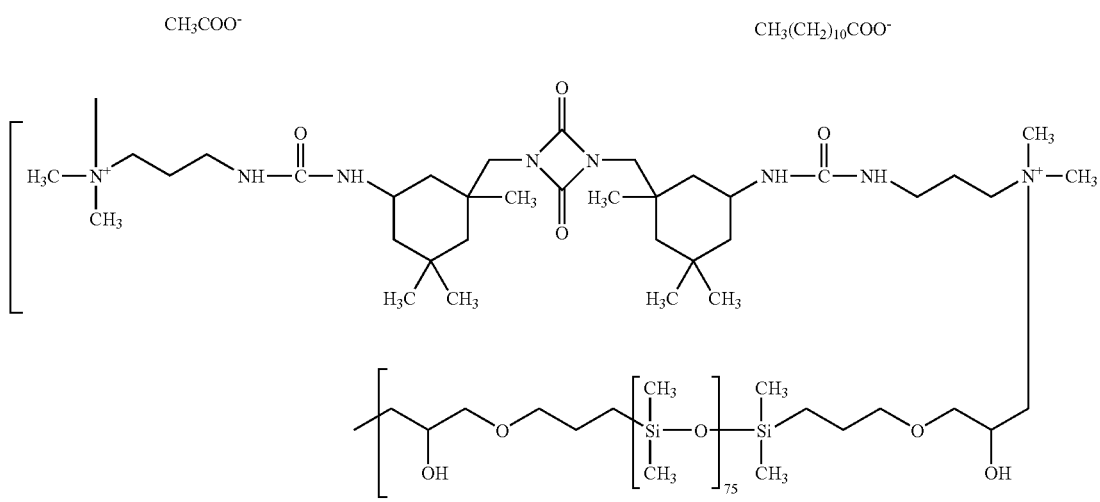

Example 2

2a) 4 g of deionized water, 1.04 g (17.27 mmol) of acetic acid, 3.45 g (17.27 mmol) of dodecanoic acid, 2.38 g (27.64 mmol of tertiary amino groups) of N,N,N',N'-tetramethyl-1,6-hexanediamine and 1.09 g (3.46 mmol of primary amino groups) of an alkylene oxide derivative which is obtainable under the trade name Jeffamin® ED 600 and has the structure H$_2$NCH(CH$_3$)CH$_2$[OCH$_2$CH(CH$_3$)]$_a$(OCH$_2$CH$_2$)$_9$[OCH$_2$CH(CH$_3$)]$_b$NH$_2$ where a+b=3.6 are dissolved in 50 ml of isopropanol.

2b) 100 g (34.54 mmol of epoxide groups) of a diepoxide of the structure

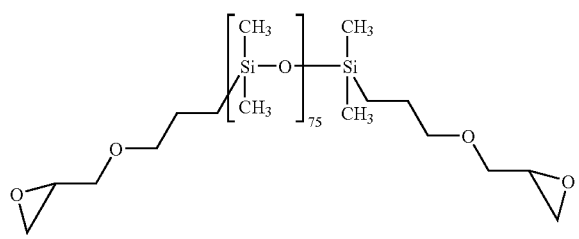

are dissolved in 100 ml of isopropanol in a 500 ml three-neck flask. 1.61 g (active content 59.5%, 3.45 mmol of NHCH$_3$ groups) of an isopropanolic solution of an aminosilane of the structure

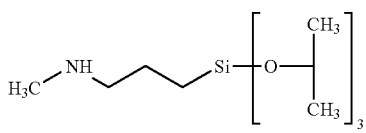

are added dropwise, and the mixture is subsequently heated to 80° C. for 8 hours. Subsequently, solution 2a) is added dropwise in its entirety and the overall mixture is heated to 82-84° C. for 10 hours. 204.7 g of a clear solution (solids content 51.3%) are obtained, which contains a polymer with the structural units

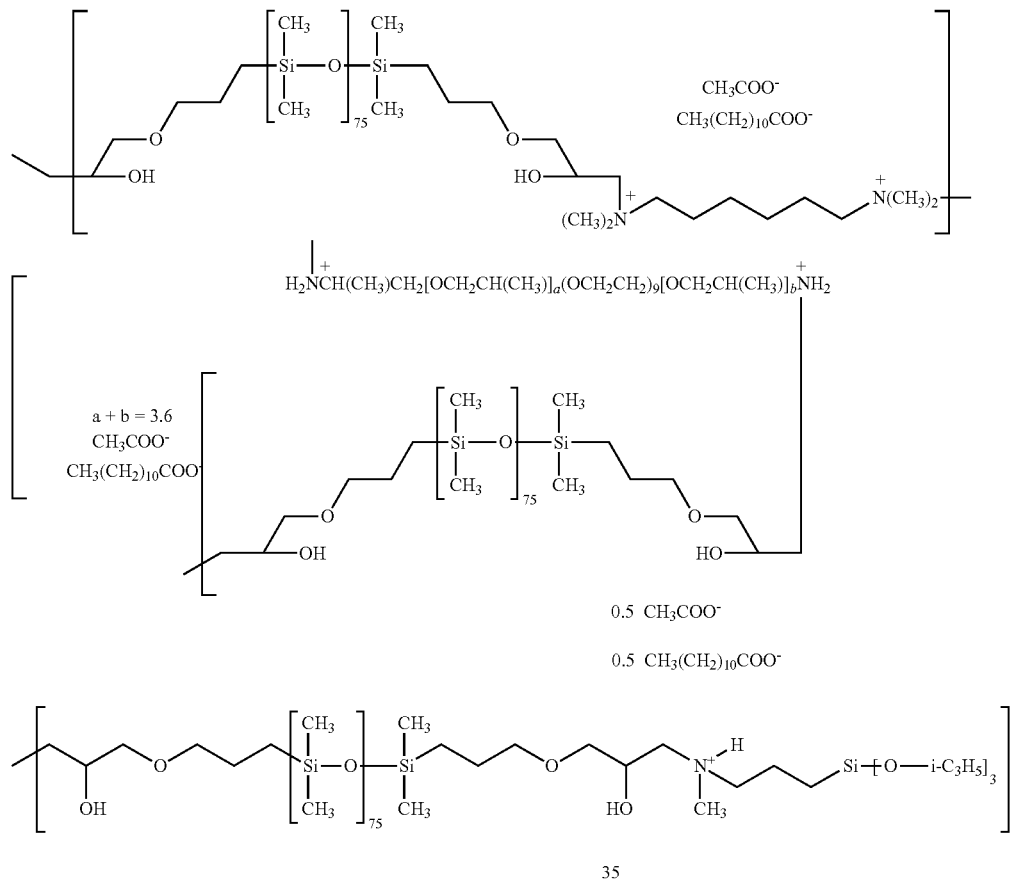
Example 3
In analogy to Example 1 and 2, a polymer with active content 82.7% is synthesized in solution, and does not contain the inventive reactive groups (I) and (II) but has structural elements including the following:
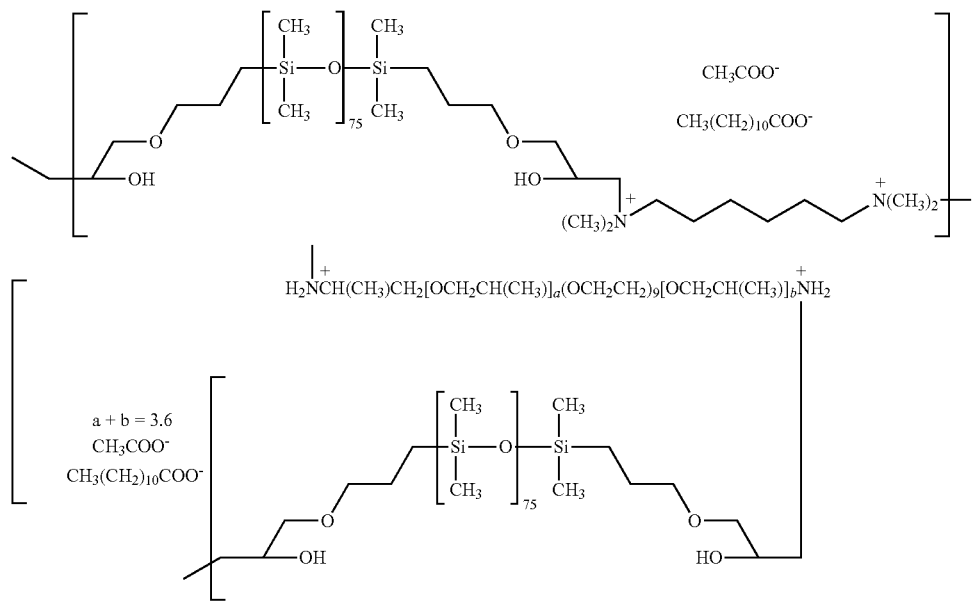
contains.

Example 4

4a) In a 500 ml three-neck flask, 1.76 g (17.26 mmol) of N,N-dimethyl-1,3-propanediamine are dissolved at room temperature in 50 ml of isopropanol. Subsequently, 4.53 g (NCO content 16%; 17.26 mmol of —NCO) of the isophorone diisocyanate dimer of the structure

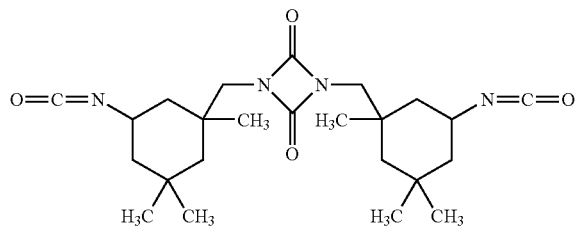

are added dropwise within a few minutes at such a rate that a clear solution is always retained. On completion of the dropwise addition, the solution is heated to 60° C. for 1 hour. A ditertiary amine of the structure

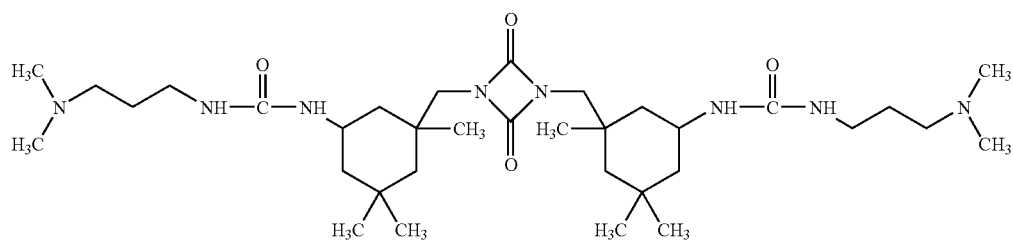

is formed.

4b) 6 g of deionized water and 3.45 g (17.26 mmol) of dodecanoic acid are added to solution 1a) and the mixture is stirred for 5 minutes.

4c) 50 g (17.26 mmol of epoxide groups) of a diepoxide of the structure

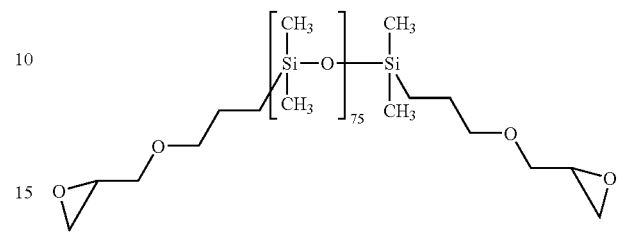

are initially charged in a three-neck flask. Subsequently, the mixture 1b) is added dropwise in its entirety with stirring. On completion of addition, the overall mixture is heated to 80-82° C. for 11 hours. After 6 hours of reaction time, the initially opaque solution becomes clear. 99 g of a light yellow, clear solution are obtained (solids content 56.5%), which contains a polymer having structural units including

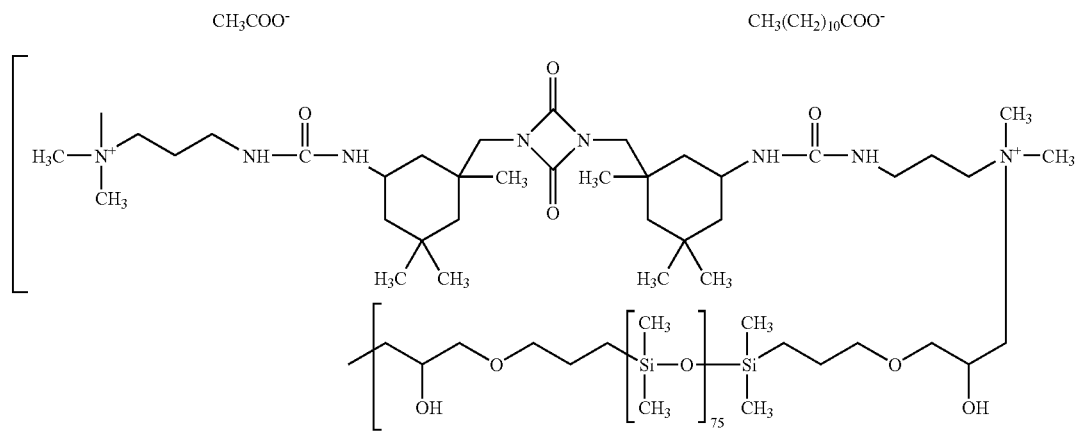

Example 5

Starting from the quaternary polysiloxanes according to Examples 1 to 3, three microemulsion concentrates of the following composition were prepared:

| Formulation 1 (F1) uretdione, inventive | Formulation 2 (F2) silane, inventive | Formulation 3 (F3) Noninventive |
|---|---|---|
| 61.9 g of Quat, Ex. 1 | 54.4 g of Quat, Ex. 2 | 52.0 g of Quat, Ex. 3 |
| 11.6 g of Renex ® 36 | 10.0 g of Renex ® 36 | 15.48 g of Renex ® 36 |
| 3.3 g of Renex ® 30 | 2.9 g of Renex ® 30 | 4.45 g of Renex ® 30 |
| 5.4 g of Crodet ® S40 | 4.7 g of Crodet ® S40 | 7.25 g of Crodet ® S40 |
| 0.75 g of acetic acid | 0.64 g of acetic acid | 1.0 g of acetic acid |
| 0.56 g of sodium acetate | 0.48 g of sodium acetate | 0.75 g of sodium acetate |
| 20.6 g of dist. water | 17.7 g of dist. water | 19.07 g of dist. water |

Renex ® 36: trade name of ICI Surfactants; tridecyl alcohol-$EO_{12}$—OH
Renex ® 30: trade name of ICI Surfactants; tridecyl alcohol-$EO_6$—OH
Crodet ® S40: trade name of Croda GmbH; stearic acid-$EO_{40}$—OH These three about 40% microemulsion concentrates were diluted with water to a uniform 11% silicone quat content in each case. Of these 11% transparent microemulsions, in each case 6 g (absolute amount of silicone quat 0.66 g) were removed, mixed intensively with 6000 ml of water and optionally additives, and utilized for textile finishing by the jet process under the following boundary conditions:

Jet type: Mathis Laboratory Jumbo-Jet

Jet pump: Setting 6 (maximum shear)

Amount of water in the jet: 6000 ml

Finishing: 20 minutes at 40° C.

Textile: 300 g of bleached cotton jersey treated with optical brightener

The cotton jersey strips finished with the formulations F1, F2 and F3 were dried in a forced-air drying cabinet at 100° C. for 15 minutes.

Subsequently, the cotton jersey strips were divided and individual pieces were subjected to the additional heat treatments listed in the table below.

| No additional heat treatment | 45 sec./ 120° C. | 120 sec./ 120° C. | 45 sec./ 150° C. | 120 sec./ 150° C. |
|---|---|---|---|---|
| F1-1 | F1-2 | F1-3 | F1-4 | F1-5 |
| F2-1 | F2-2 | F2-3 | F2-4 | F2-5 |
| F3-1 | F3-2 | F3-3 | F3-4 | F3-5 |

The individual cotton jersey pieces were then washed 5× for 20 minutes at 40° C. with a silicate-free light-duty laundry detergent (1.7 g of laundry detergent/liter of wash liquor).

Subsequently, 5 test subjects independently assessed the rank order of the cotton jersey pieces with regard to softness.

Within the three groups F1-1 to F1-5, F2-1 to F2-5 and F3-1 to F3-5, the softest jersey strips were initially determined to be F1-5, F2-1 and F3-4.

These selected three strips were subjected to an evaluation in a direct comparison by the 5 test subjects, the softest textile piece receiving the mark 1 and the hardest textile piece the mark 3.

In parallel, the droplet absorption time was determined as a measure of the hydrophilicity.

The table which follows summarizes the results.

| Textile piece | Ø softness mark (5 test subjects) | Droplet absorption time (seconds) |
|---|---|---|
| F1-5 | 1.2 | 2 |
| F2-1 | 1.8 | 2 |
| F3-4 | 3.0 | 1 |

* Droplet absorption time

The data on the softnesses of the textile pieces F1-5 and F2-1 after 5 wash cycles demonstrate that the incorporation of inventive structural elements further improves the permanence of the textile finishing and hence the softness. In addition, the highly hydrophilic character of the finish can be maintained.

The invention claimed is:

1. Amino- and/or ammoniopolysiloxane compounds and salts thereof, comprising
   (a) at least one functional group having formula (I):

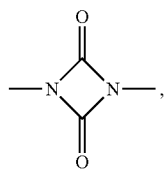

(I)

(b) at least three units selected from the units Q and V,
      wherein Q is at least one di-, tri- and/or tetravalent amino and/or ammonium group which is not bonded to V via a carbonyl carbon atom, and
      V is at least one organic unit which is bonded to the Q units via carbon, with the proviso that at least one of the units V contains a polyorganosiloxane radical, and
   wherein at least one of the V groups comprises a functional group of the formula (I)

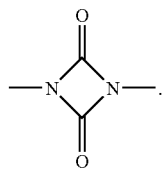

(I)

2. The compound according to claim 1, wherein the at least one functional group (I) has the formula (Ia)

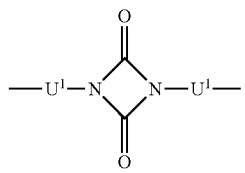

(Ia)

wherein
U¹ is selected from the group consisting of divalent radicals of the formulae:

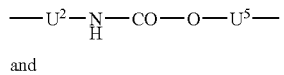
(Ic)

and

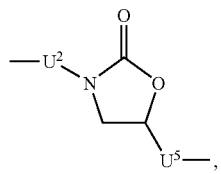
(Id)

where
U² is bonded to the nitrogen atom of the functional group of the formula (I), and U² is a divalent, straight-chain, cyclic or branched, saturated, unsaturated or aromatic hydrocarbon radical which has up to 100 carbon atoms and may contain one or more —O— groups, U³ is hydrogen or a monovalent, straight-chain, cyclic or branched, saturated, unsaturated or aromatic hydrocarbon radical which has up to 100 carbon atoms and may contain one or more —O— groups and be substituted by OH, consisting of —W—Si(OR)$_{3-a}$(RN wherein R, R' are each as defined above and a=from 0 to 2 and W is a divalent, straight-chain, cyclic or branched, saturated, unsaturated or aromatic hydrocarbon radical which has up to 100 carbon atoms and may contain one or more —C(O)—, —O—, —NH—, —S— groups, and may optionally be substituted by hydroxyl groups, U⁴ and U⁵ are each divalent straight-chain, cyclic or branched, saturated, unsaturated or aromatic hydrocarbon radicals which have up to 1000 carbon atoms and may optionally contain one or more groups selected from —O—, —C(O)—,

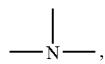

—NR²— wherein R² is as defined above, and which may optionally be substituted by one or more hydroxyl groups, with the proviso that the

and —NR²— groups are bonded to a carbonyl carbon atom.

3. Amino- and/or ammoniopolysiloxane compounds and salts thereof, comprising at least one functional group selected from the group consisting of formula (I) and formula (II):

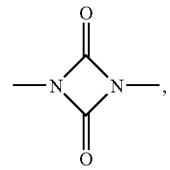
(I)

(II)

wherein a is an integer from 0 to 2 and R and R' may be the same or different from one another and each represents an organic radical, and wherein the group of the formula (II) is bonded to a carbon atom.

4. The compound according to claim 3 having at least three units selected from the units Q and V, wherein Q is at least one di-, tri- and/or tetravalent amino and/or ammonium group which is not bonded to V via a carbonyl carbon atom, and V is at least one organic unit which is bonded to the Q units via carbon, with the proviso that at least one of the units V contains a polyorganosiloxane radical.

5. The compound according to claim 4, comprising at least two units V which contain a polyorganosiloxane radical.

6. The compound according to claim 4, comprising at least two Q units.

7. The compound according to claim 4, wherein the unit Q is selected from the group consisting of:
—NR¹—,
—N⁺R¹₂,
a saturated or unsaturated, diamino-functional heterocycle which is optionally substituted by further substituents and has a formula selected from the group consisting of:

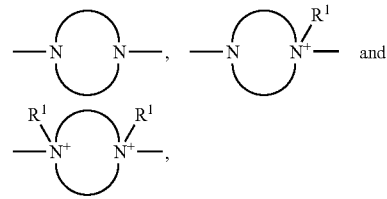

and also
an aromatic, optionally substituted, diamino-functional heterocycle of the formula:

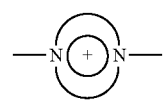

a trivalent radical of the formula:

a trivalent radical of the formula:

or a tetravalent radical of the formula

wherein R¹ is in each case hydrogen or a monovalent organic radical, where Q is not bonded to a carbonyl carbon atom.

8. The compound according to claim 3, comprising at least one quaternary ammonium group.

9. The compound according to claim 3, comprising at least two quaternary ammonium groups.

10. The compound according to claim 3, comprising at least one R¹ radical of the formula (VIIIa)

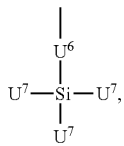

wherein
- U⁶ is a divalent straight-chain, cyclic or branched, saturated, unsaturated or aromatic hydrocarbon radical which has up to 100 carbon atoms and may optionally contain one or more groups selected from —O—, —C(O)—, —NH— and —NU⁸—, or may optionally be substituted by one or more hydroxyl groups, wherein U⁸ is hydrogen or a monovalent, straight-chain, cyclic or branched, saturated, unsaturated or aromatic hydrocarbon radical which has up to 100 carbon atoms and may contain one or more —O— groups and be substituted by OH, with the proviso that —NH— and —NU⁸-is bonded to a carbonyl and/or thiocarbonyl carbon atom, and
- U⁷ is a monovalent, straight-chain, cyclic or branched, saturated, unsaturated or aromatic hydrocarbon radical which has up to 20 carbon atoms and may contain one or more —O— groups and be substituted by OH, with the proviso that the U⁷ radicals may be the same or different and at least one U⁷ radical per silicon atom is bonded to the silicon atom via —O—.

11. A process for preparing textile softening formulations comprising combining at least one compound according claim 3, with a laundry detergent.

12. An aqueous emulsion comprising the formulation according to claim 3.

13. Amino- and/or ammoniopolysiloxane compounds and salts thereof, comprising at least one functional group selected from the group consisting of formula (I) and formula (II):

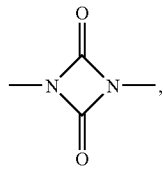  (I)

  (II)

wherein a is an integer from 0 to 2 and R and R' may be the same or different from one another and each represents an organic radical, and wherein said amino- and/or ammoniopolysiloxane compounds have at least three units selected from the units Q and V, wherein Q is at least one di-, tri- and/or tetravalent amino and/or ammonium group which is not bonded to V via a carbonyl carbon atom, and V is at least one organic unit which is bonded to the Q units via carbon, with the proviso that at least one of the units V contains a polyorganosiloxane radical, wherein the unit Q is selected from the group consisting of:
—NR¹—,
—N⁺R¹₂,
a saturated or unsaturated, diamino-functional heterocycle which is optionally substituted by further substituents and has a formula selected from the group consisting of:

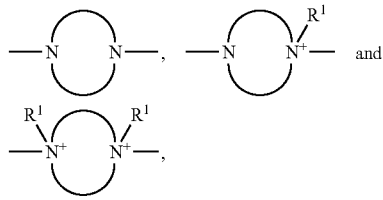

and also
an aromatic, optionally substituted, diamino-functional heterocycle of the formula:

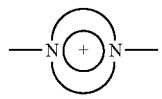

a trivalent radical of the formula:

a trivalent radical of the formula:

or a tetravalent radical of the formula

wherein $R^1$ is in each case hydrogen or a monovalent organic radical, where Q is not bonded to a carbonyl carbon atom, wherein said amino- and/or ammoniopolysiloxane compounds comprises a which has an $R^1$ radical which has a group of the formula (II).

14. The compound according to claim 13, comprising at least one quaternary ammonium group.

15. The compound according to claim 13, comprising at least two quaternary ammonium groups.

16. The compound according to claim 13, wherein the unit V is selected from polyvalent, straight-chain, cyclic or branched, saturated, unsaturated or aromatic hydrocarbon radical which has up to 1000 carbon atoms (where the carbon atoms of the optionally present polyorganosiloxane radical are not counted), may optionally contain one or more groups selected from

—O—, —C(O)—, —C(S)—,

—NR²— wherein $R^2$ is hydrogen, a monovalent, straight-chain, cyclic or branched, saturated, unsaturated or aromatic hydrocarbon radical which has up to 300 carbon atoms, may contain one or more groups selected from —O—, —NH—, —C(O)— and —C(S)—, and may optionally be substituted by one or more substituents selected from the group which consists of a hydroxyl group, an optionally substituted heterocyclic group polyether radicals, polyetherester radicals, polyorganosiloxanyl radicals and —Si(OR)₃₋ₐ(R')ₐ, wherein a, R and R' are each as defined above, where, when a plurality of —NR²— groups are present, they may be the same or different, and with the proviso that the —NR²— group bonds to a carbonyl and/or thiocarbonyl carbon atom,

and polyorganosiloxane radicals, and may optionally be substituted by one or more hydroxyl groups and/or groups of the formula (II)

—Si(OR)₃₋ₐ(R')ₐ wherein a, R and R' are each as defined above,
and with the proviso that at least one V radical contains at least one polyorganosiloxane radical,
and wherein the polyvalent Q and V groups bonded to one another are saturated terminally by monovalent organic radicals.

17. The compound according to claim 13, comprising at least one unit V which contains a group of the formula (III)

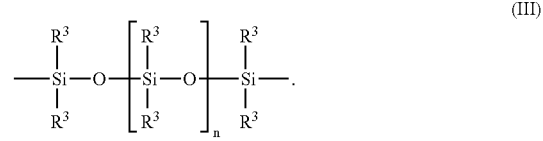

18. The compound according to claim 13, comprising at least one $R^1$ radical of the formula (VIIIa)

wherein
U⁶ is a divalent straight-chain, cyclic or branched, saturated, unsaturated or aromatic hydrocarbon radical which has up to 100 carbon atoms and may optionally contain one or more groups selected from —O—, —C(O)—, —NH— and —NU⁸—, or may optionally be substituted by one or more hydroxyl groups, wherein U⁸ is hydrogen or a monovalent, straight-chain, cyclic or branched, saturated, unsaturated or aromatic hydrocarbon radical which has up to 100 carbon atoms and may contain one or more —O— groups and be substituted by OH, with the proviso that —NH— and —NU⁸—is bonded to a carbonyl and/or thiocarbonyl carbon atom, and U⁷ is a monovalent, straight-chain, cyclic or branched, saturated, unsaturated or aromatic hydrocarbon radical which has up to 20 carbon atoms and may contain one or more —O— groups and be substituted by OH, with the proviso that the U⁷ radicals may be the same or different and at least one U⁷ radical per silicon atom is bonded to the silicon atom via —O—.

19. A process for preparing textile softening formulations comprising combining at least one compound according claim 13, with a laundry detergent.

20. An aqueous emulsion comprising the formulation according to claim 13.

21. Amino- and/or ammoniopolysiloxane compounds and salts thereof, comprising at least one functional group selected from the group consisting of formula (I) and formula (II):

wherein a is an integer from 0 to 2 and R and R' may be the same or different from one another and each represents an organic radical, and wherein said amino- and/or ammoniopolysiloxane compounds contain at least two repeat units of the formula (IV):

-[Q-V]— (IV)

wherein Q is at least one di-, tri- and/or tetravalent amino and/or ammonium group which is not bonded to V via a carbonyl carbon atom, and V is at least one organic unit which is bonded to the Q units via carbon, with the proviso that at least one of the units V contains a polyorganosiloxane radical, and wherein the compound further comprises at least one radical $R^1$ of the formula (VIIIa)

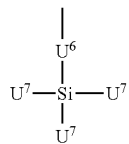
(VIIIa)

wherein $U^6$ is a divalent straight-chain, cyclic or branched, saturated, unsaturated or aromatic hydrocarbon radical which has up to 100 carbon atoms and may optionally contain one or more groups selected from —O—, —C(O)—, —NH— and —$NU^8$— or may optionally be substituted by one or more hydroxyl groups, wherein $U^8$ is hydrogen or a monovalent, straight-chain, cyclic or branched, saturated, unsaturated or aromatic hydrocarbon radical which has up to 100 carbon atoms and may contain one or more —O— groups and be substituted by OH, with the proviso that —NH— and —$NU^8$— is bonded to a carbonyl and/or thiocarbonyl carbon atom, and $U^7$ is a monovalent, straight-chain, cyclic or branched, saturated, unsaturated or aromatic hydrocarbon radical which has up to 20 carbon atoms and may contain one or more —O— groups and be substituted by OH, with the proviso that the $U^7$ radicals may be the same or different and at least one $U^7$ radical per silicon atom is bonded to the silicon atom via —O—.

* * * * *